United States Patent
Law et al.

(10) Patent No.: US 12,263,223 B2
(45) Date of Patent: Apr. 1, 2025

(54) METHOD OF TREATING DISEASES OF THE KIDNEY AND URINARY TRACT BY ADMINISTERING A PEPTIDE-LINKED THERAPEUTIC AGENT

(71) Applicants: Cornell University, Ithaca, NY (US); Tu Therapeutics Inc., New York, NY (US)

(72) Inventors: Shek Hang Benedict Law, New York, NY (US); Vanessa Bellat, New York, NY (US); Benjamin Byung-min Choi, Englewood Cliffs, NJ (US)

(73) Assignees: Cornell University, Ithaca, NY (US); Tu Therapeutics Inc., New York, NY (US)

( * ) Notice: Subject to any disclaimer, the term of this patent is extended or adjusted under 35 U.S.C. 154(b) by 165 days.

(21) Appl. No.: 18/095,753

(22) Filed: Jan. 11, 2023

(65) Prior Publication Data
US 2023/0190948 A1    Jun. 22, 2023

Related U.S. Application Data

(63) Continuation of application No. 17/556,714, filed on Dec. 20, 2021, now Pat. No. 11,571,481.

(60) Provisional application No. 63/254,754, filed on Oct. 12, 2021, provisional application No. 63/128,509, filed on Dec. 21, 2020.

(51) Int. Cl.
| | |
|---|---|
| *A61K 47/65* | (2017.01) |
| *A61K 45/06* | (2006.01) |
| *A61K 47/18* | (2017.01) |
| *A61P 13/10* | (2006.01) |
| *A61P 35/00* | (2006.01) |

(52) U.S. Cl.
CPC .............. *A61K 47/65* (2017.08); *A61K 45/06* (2013.01); *A61K 47/183* (2013.01); *A61P 13/10* (2018.01); *A61P 35/00* (2018.01)

(58) Field of Classification Search
CPC .............................. A61K 47/65; A61K 47/183
See application file for complete search history.

(56) References Cited

U.S. PATENT DOCUMENTS

| | | |
|---|---|---|
| 6,844,318 B2 | 1/2005 | Copeland et al. |
| 7,438,900 B2 | 10/2008 | Piccariello et al. |
| 8,227,403 B2 | 7/2012 | Arumugham et al. |
| 8,445,528 B2 | 5/2013 | Baker, Jr. et al. |
| 8,598,314 B2 | 12/2013 | Ghosh et al. |
| 8,741,863 B2 | 6/2014 | Moulton et al. |
| 8,759,295 B2 | 6/2014 | Ghosh et al. |
| 8,889,635 B2 | 11/2014 | Baker, Jr. et al. |
| 9,750,818 B2 | 9/2017 | Alargova et al. |
| 11,065,336 B2 | 7/2021 | Crowther et al. |
| 11,111,271 B2 | 9/2021 | Cundy et al. |
| 11,571,481 B2 | 2/2023 | Law et al. |
| 2003/0130272 A1 | 7/2003 | Mincher et al. |
| 2007/0134762 A1 | 6/2007 | Arumugham et al. |
| 2016/0058881 A1 | 3/2016 | DiMarchi et al. |
| 2016/0114054 A1 | 4/2016 | Kuebelbeck et al. |
| 2016/0199505 A1 | 7/2016 | Kuebelbeck et al. |
| 2017/0348337 A1 | 12/2017 | Schmidt et al. |
| 2020/0353088 A1 | 11/2020 | Harris et al. |
| 2021/0138077 A1 | 5/2021 | Bindman et al. |
| 2022/0193248 A1 | 6/2022 | Law et al. |
| 2023/0190948 A1 | 6/2023 | Law et al. |

FOREIGN PATENT DOCUMENTS

| | | |
|---|---|---|
| EP | 2714092 B1 | 7/2020 |
| WO | WO-2022/140289 A1 | 6/2022 |
| WO | WO-2024/118760 A1 | 6/2024 |

OTHER PUBLICATIONS

Akizawa et al., "Effect of molecular charges on renal uptake of 111In-DTPA-conjugated peptides," Nuclear Medicine and Biology, 28(7): 761-768 (2001).
Argyros et al., "Peptide-Drug Conjugate GnRH-Sunitinib Targets Angiogenesis Selectively at the Site of Action to Inhibit Tumor Growth," Cancer Res, 76(5): 1181-1192 (2016).
Bellat et al., "A Urinary Drug-Disposing Approach as an Alternative to Intravesical Chemotherapy for Treating Nonmuscle Invasive Bladder Cancer, " Cancer Research, 82(7): 1409-1422 (2022).
Geng et al., "Peptide-Drug Conjugate Linked via a Disulfide Bond for Kidney Targeted Drug Delivery," Bioconjugate Chem., 23(6): 1200-1210 (2012).
Ghosh et al., "Targeted therapies in urothelial carcinoma," Current Opinion in Oncology, 26(3): 305-320 (2014).
Huang et al., "The effect of size, charge, and peptide ligand length on kidney targeting by small, organic nanoparticles," Bioengineering & Translational Medicine, 5(3): e10173 (2020).
International Search Report and Written Opinion for International Application No. PCT/US2021/064419 dated Mar. 29, 2022.
Lenhard et al., "In Vivo Imaging of Small Molecular Weight Peptides for Targeted Renal Drug Delivery: A Study in Normal and Polycystic Kidney Diseased Mice," Journal of Pharmacology and Experimental Therapeutics, 370(3): 786-795 (2019).
Liu et al., "Passive Tumor Targeting of Renal-Clearable Luminescent Gold Nanoparticles: Long Tumor Retention and Fast Normal Tissue Clearance," Journal of the American Chemical Society, 135(13): 4978-4981 (2013).
Wischnjow et al., "Renal Targeting: Peptide-Based Drug Delivery to Proximal Tubule Cells," Bioconjugate Chem., 27(4): 1050-1057 (2016).
International Search Report and Written Opinion for International Application No. PCT/US23/81581 dated Apr. 11, 2024.

*Primary Examiner* — Robert S Landsman
(74) *Attorney, Agent, or Firm* — Foley Hoag LLP; Lucas P. Watkins; Lawrence P. Tardibono

(57) ABSTRACT

The present disclosure relates to a systemically administered peptide delivery platform that biodistributes to the kidney or urinary tract. The disclosure further relates to methods of treating a disease of the kidney or urinary tract in a subject in need thereof.

19 Claims, 35 Drawing Sheets
(24 of 35 Drawing Sheet(s) Filed in Color)

| Name | Peptide Sequence | Net charges pH = 7.4 |
|---|---|---|
| BDD | $NH_2$-BDDBDDBDDBDD-$CONH_2$ | -8 |
| Bdd | $NH_2$-BddBddBddBdd-$CONH_2$ (D-configuration) | -8 |
| BKD | $NH_2$-BKDBKDBKDBKD-$CONH_2$ | 0 |
| BKK | $NH_2$-BKKBKKBKKBKK-$CONH_2$ | +8 |
| $PEG_3DD$ | $NH_2$-($PEG_3$)DD($PEG_3$)DD($PEG_3$)DD($PEG_3$)DD-$CONH_2$ | -8 |

| Parameters | BDD | Bdd | BKD | BKK | PEG₃DD | Free ⁸⁹Zr |
|---|---|---|---|---|---|---|
| $k_{10}$ (h⁻¹) | 5.02 ± 0.95 | 5.06 ± 1.94 | 6.06 ± 1.07 | 2.03 ± 0.68 | 4.93 ± 1.51 | 0.15 ± 0.02 |
| $k_{12}$ (h⁻¹) | 2.01 ± 0.98 | 1.52 ± 0.42 | 2.55 ± 0.98 | 3.83 ± 0.81 | 2.52 ± 0.29 | 1.65 ± 0.86 |
| $k_{21}$ (h⁻¹) | 2.11 ± 0.47 | 1.31 ± 0.47 | 2.09 ± 1.33 | 0.71 ± 0.25 | 1.76 ± 0.98 | 1.23 ± 0.57 |
| $t_{1/2\alpha}$ (h) | 0.09 ± 0.03 | 0.10 ± 0.02 | 0.08 ± 0.02 | 0.11 ± 0.03 | 0.10 ± 0.06 | 0.28 ± 0.12 |
| $t_{1/2\beta}$ (h) | 0.46 ± 0.09 | 0.53 ± 0.21 | 0.65 ± 0.30 | 3.12 ± 0.68 | 0.64 ± 0.38 | 11.62 ± 1.82 |
| $C_0$ (μCi·mL⁻¹) | 1.43 ± 0.43 | 1.12 ± 0.51 | 3.74 ± 1.12 | 1.60 ± 0.58 | 2.20 ± 0.74 | 9.73 ± 1.28 |
| $V_d$ (mL) | 11.53 ± 2.98 | 21.24 ± | 5.77 ± 1.94 | 12.55 ± 3.37 | 10.33 ± 2.31 | 2.08 ± 0.25 |
| CL (mL·h⁻¹) | 64.29 ± 12.16 | 71.23 ± 13.72 | 33.46 ± 4.80 | 27.09 ± 4.66 | 46.22 ± 5.81 | 0.30 ± 0.02 |
| $V_{d2}$ (mL) | 12.03 ± 4.67 | 12.17 ± 9.45 | 7.86 ± 2.88 | 60.61 ± 14.14 | 10.32 ± 6.41 | 2.73 ± 0.36 |
| $CL_2$ (mL·h⁻¹) | 26.12 ± 10.85 | 33.06 ± 17.47 | 13.98 ± 5.06 | 46.89 ± 9.24 | 16.44 ± 3.21 | 3.28 ± 1.32 |
| AUC (h·μCi·mL⁻¹) | 0.33 ± 0.06 | 0.29 ± 0.06 | 0.60 ± 0.08 | 0.73 ± 0.20 | 0.43 ± 0.05 | 51.72 ± 1.24 |
| MRT (h) | 0.35 ± 0.06 | 0.36 ± 0.17 | 0.41 ± 0.09 | 1.96 ± 0.73 | 0.45 ± 0.21 | 16.23 ± 2.51 |
| $V_{ss}$ (mL) | 23.57 ± 2.51 | 22.59 ± 4.27 | 13.63 ± 4.26 | 74.80 ± 12.50 | 20.65 ± 7.65 | 4.81 ± 0.53 |

|  | CK-55 | | | CK-DM1 | | | CK-DM1-RdR | | | CK-65 | | |
|---|---|---|---|---|---|---|---|---|---|---|---|---|
|  | M1 | M2 | M3 | M1 | M2 | M3 | M1 | M2 | M3 | M1 | M2 | M3 |
| RBC (M/µL) | 8.55 | 8.56 | 9.1 | 9.23 | 9.61 | 7.84 | 8.02 | 8.69 | 9.48 | 9.45 | 8.79 | 9.31 |
| HGB (g/dL) | 13.7 | 13.8 | 14.3 | 14.3 | 13.8 | 11.9 | 12.7 | 14.1 | 15.2 | 14.9 | 14 | 14.9 |
| HCT (%) | 42.6 | 42.6 | 44.8 | 45.1 | 45.4 | 43.4 | 39.7 | 42.9 | 47.6 | 44.5 | 42.8 | 45.9 |
| MCV (fL) | 49.8 | 49.8 | 49.2 | 48.2 | 47.2 | 46.6 | 49.5 | 49.4 | 49 | 47.1 | 48.7 | 49.3 |
| MCH (pg) | 16 | 16.1 | 15.7 | 15.5 | 14.9 | 15.2 | 15.8 | 16.2 | 15.7 | 15.8 | 15.9 | 16 |
| MCHC (g/dL) | 32.2 | 32.4 | 31.9 | 31.7 | 31.5 | 32.6 | 32 | 32.9 | 31.9 | 33.5 | 32.7 | 32.5 |
| RDW-SD (fL) | 28.3 | 28.4 | 27.5 | 30.2 | 29.5 | 29.1 | 28.8 | 28.9 | 28.8 | 26 | 29.4 | 29.3 |
| RDW-CV (%) | 21.7 | 22.4 | 22.4 | 24.1 | 24.7 | 23.8 | 22.1 | 23.1 | 23.7 | 22.9 | 23.6 | 24.5 |
| RET# (K/µL) | 626.5 | 498.2 | 469.6 | 1247 | 1134 | 1646.1 | 624 | 517.6 | 619.5 | 620.4 | 611.8 | 629.4 |
| RET (%) | 5.41 | 5.82 | 6.63 | 13.51 | 11.8 | 11.3 | 7.78 | 5.46 | 6.38 | 6.66 | 6.96 | 6.76 |
| PLT (K/µL) | 756 | 799 | 669 | 931 | 938 | 1163 | 831 | 504 | 850 | 135 | 169 | 121 |
| PDW (fL) | 10.2 | 7.9 | 10.6 | 9.6 | 10 | 9.2 | 10 | 7.2 | 8.3 | 8.9 | 8.1 | 7.7 |
| MPV (fL) | 7.5 | 6.7 | 7.4 | 7.3 | 7.7 | 7.2 | 7.6 | 6.6 | 7 | 7.9 | 8.6 | 6.5 |
| WBC# (K/µL) | 7.91 | 7.23 | 6.74 | 8.25 | 10.45 | 9.19 | 7.68 | 7.01 | 7.58 | 4.36 | 4.08 | 4.41 |
| NEUT# (K/µL) | 1.61 | 1.28 | 1.26 | 3.08 | 2.31 | 3.2 | 1.12 | 0.93 | 0.88 | 1.02 | 1.14 | 1.01 |
| LYMPH# (K/µL) | 6.09 | 5.7 | 4.24 | 5.34 | 4.11 | 3.72 | 6.34 | 5.52 | 4.96 | 2.9 | 2.75 | 3.16 |
| MONO# (K/µL) | 0.13 | 0.12 | 0.11 | 1.39 | 1.02 | 1.11 | 0.11 | 0.1 | 0.18 | 0.41 | 0.16 | 0.2 |
| EO# (K/µL) | 0.08 | 0.13 | 0.12 | 0.13 | 0.13 | 0.07 | 0.11 | 0.16 | 0.08 | 0.03 | 0.04 | 0.09 |
| BASO# (K/L) | 0 | 0 | 0.01 | 0.02 | 0.01 | 0.01 | 0 | 0 | 0 | 0 | 0 | 0 |
| NEUT (%) | 20.4 | 17.7 | 11.5 | 25.2 | 31.7 | 45.7 | 14.6 | 13.3 | 14.4 | 23.4 | 28 | 22.9 |
| LYMPH (%) | 77 | 78.8 | 84.9 | 60.7 | 57.2 | 63.5 | 82.6 | 78.7 | 81.3 | 66.5 | 67.4 | 71.7 |
| MONO (%) | 1.6 | 1.7 | 1.6 | 20.5 | 9.8 | 13.2 | 1.4 | 3.7 | 3 | 4 | 3.9 | 3.4 |
| EO (%) | 1 | 1.8 | 1.8 | 1 | 1.2 | 0.5 | 1.4 | 2.3 | 1.3 | 0.7 | 0.7 | 2 |
| BASO (%) | 0 | 0 | 0.1 | 0 | 0.1 | 0.1 | 0 | 0 | 0 | 0 | 0 | 0 |

FIG. 10

|  | M1 | M2 | M3 | M1 | M2 | M3 | M1 | M2 | M3 | M1 | M2 | M3 |
|---|---|---|---|---|---|---|---|---|---|---|---|---|
| BUN (mg/dL) | 15 | 21 | 17 | 32 | 30 | 27 | 21 | 13 | 19 | 28 | 27 | 29 |
| CREA (mg/dL) | 0.24 | 0.28 | 0.26 | 0.19 | 0.14 | 0.18 | 0.22 | 0.23 | 0.22 | 0.24 | 0.19 | 0.22 |
| BUN/CREA Ratio | 62.5 | 75 | 73.9 | 168.4 | 178.6 | 142.1 | 86.4 | 56.5 | 91.3 | 116.7 | 126.1 | 77.3 |
| ALP (U/L) | 137 | 130 | 135 | 202 | 167 | 139 | 130 | 153 | 147 | 88 | 87 | 101 |
| ALT (U/L) | 42 | 28 | 32 | 643 | 512 | 328 | 27 | 33 | 30 | 89 | 87 | 64 |
| AST (U/L) | 126 | 107 | 86 | 517 | 741 | 561 | 108 | 78 | 91 | 175 | 290 | 338 |
| GGT (U/L) | 0 | 0 | 0 | 0 | 0 | 0 | 0 | 0 | 0 | 0 | 0 | 0 |
| TBIL (mg/dL) | 0.1 | 0.1 | 0.1 | 0.2 | 0.2 | 0.2 | 0.1 | 0.1 | 0.1 | 0.2 | 0.2 | 0.2 |
| DBIL (mg/dL) | 0 | 0 | 0 | 0 | 0 | 0 | 0 | 0 | 0 | 0 | 0 | 0 |
| IBIL (mg/dL) | 0.1 | 0.1 | 0.1 | 0.2 | 0.2 | 0.2 | 0.1 | 0.1 | 0.1 | 0.2 | 0.2 | 0.2 |
| TP (g/dL) | 5.2 | 5.1 | 5 | 5.5 | 5.6 | 5.5 | 5.1 | 5.3 | 5.3 | 4.9 | 5 | 5.5 |
| ALB (g/dL) | 3.3 | 3.2 | 3.2 | 3.4 | 3.3 | 3.6 | 3.3 | 3.4 | 3.4 | 3.3 | 3.1 | 3.5 |
| GLOB (g/dL) | 1.9 | 1.9 | 1.8 | 2.1 | 2.1 | 2.2 | 1.8 | 1.9 | 1.9 | 1.9 | 2 | 2 |
| A/G Ratio | 1.7 | 1.7 | 1.8 | 1.8 | 1.6 | 1.5 | 1.7 | 1.8 | 1.8 | 2.1 | 1.6 | 1.8 |
| P (mg/dL) | 9.4 | 8.2 | 8 | 9.1 | 9.9 | 10.6 | 9.1 | 9.5 | 9.2 | 9.4 | 8.5 | 7.9 |
| Ca (mg/dL) | 10.2 | 10.2 | 10.3 | 10.3 | 11.1 | 11.1 | 9.8 | 9.9 | 10.2 | 9.8 | 10 | 10.1 |
| GLU (mg/dL) | 175 | 163 | 201 | 241 | 199 | 263 | 185 | 182 | 174 | 150 | 172 | 146 |
| CHOL (mg/dL) | 86 | 86 | 84 | 85 | 78 | 64 | 79 | 90 | 81 | 64 | 96 | 88 |
| TRIG (mg/dL) | 151 | 142 | 162 | 180 | 144 | 206 | 146 | 147 | 174 | 108 | 144 | 134 |
| CK (U/L) | 386 | 327 | 463 | 697 | 814 | 1043 | 372 | 369 | 348 | 2046 | 1445 | 1503 |
| TCO2 (mEq/L) | 23 | 24 | 22 | 10 | 14 | 12 | 23 | 19 | 22 | 19 | 17 | 20 |
| Na (mEq/L) | 157 | 157 | 153 | 154 | 151 | 154 | 156 | 154 | 156 | 160 | 158 | 155 |
| K (mEq/L) | 7.8 | 7.6 | 8 | 8.2 | 7.2 | 9.5 | 7.8 | 8 | 8.5 | 8.9 | 9.2 | 8.3 |
| CL (mEq/L) | 112 | 113 | 111 | 113 | 112 | 117 | 115 | 109 | 114 | 118 | 120 | 116 |
| Na/K | 20 | 21 | 19 | 19 | 21 | 16 | 20 | 19 | 18 | 18 | 17 | 19 |
| Anion Gap | 30 | 28 | 28 | 41 | 32 | 35 | 26 | 28 | 28 | 32 | 32 | 27 |

FIG. 11

METHOD OF TREATING DISEASES OF THE KIDNEY AND URINARY TRACT BY ADMINISTERING A PEPTIDE-LINKED THERAPEUTIC AGENT

RELATED APPLICATIONS

This application is a continuation of U.S. patent application Ser. No. 17/556,714, filed Dec. 20, 2021, which claims the benefit of U.S. Provisional Application Nos. 63/128,509, filed Dec. 21, 2020, and 63/254,754, filed Oct. 12, 2021, the contents of each of which are fully incorporated by reference herein.

STATEMENT REGARDING FEDERALLY SPONSORED RESEARCH

This invention was made with government support under Grant CA222802 awarded by the National Institutes of Health. The government has certain rights in the invention.

BACKGROUND

Diseases of the kidney and urinary tract cause significant morbidity and mortality. For example, urothelial carcinoma, the most common type of bladder cancer (BC), is one of the leading cancers in the United States. Most BCs are non-muscle invasive and superficial in nature. The standard treatments involve instillation of chemotherapeutic/immunotherapeutic agents in the bladder after initial surgical resection of the tumor. These drugs are often administered via catheterization of the urethra into the bladder, also known as intravesical therapy (ITT). Despite evidence of ITT's clinical efficacy, disease recurrence rate remains high, up to 50%. This can be caused by incomplete drug delivery, as the administered drug can only be retained in the bladder for a limited time. Furthermore, urothelial carcinoma can recur throughout the entire urothelium (renal pelvis, ureter, and bladder). Since ITT only delivers drugs to the bladder, any tumors in the ureter or renal pelvis cannot be reached. ITT also requires invasive catheterization, which can cause pain, infection, urinary symptoms, poor patient compliance, and ultimately lead to treatment discontinuation. There remains a need to identify systems that overcome the drug delivery barriers of current ITT for treatment of diseases of the kidney and urinary tract without requiring an invasive procedure or surgery. Such systems should deliver systemically administered therapies to the urinary system without systemic toxicity and result in prolonging the contact time between the drug and the urinary system, providing a more effective treatment for diseases such as urothelial carcinoma.

SUMMARY OF THE INVENTION

In certain embodiments, the present disclosure provides a compound represented by formula (I):

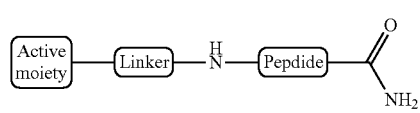

(I)

or a pharmaceutically acceptable salt thereof, wherein the peptide is a peptide targeted for renal clearance.

In certain aspects, the present disclosure provides a method of treating cancer, comprising administering to a patient in need thereof a compound or composition of the disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) Conventional intravesical chemotherapy (ITC) is invasive, and the drug delivery is limited to bladder. Bdd is designed to carry multiple negative charges that minimize off-targeting delivery and facilitates renal excretion after intravenous (i.v.) administration. When used as a drug carrier, Bdd promotes drug deposition into the entire urothelial system and provides a continuous drug excretion for a more comprehensive treatment. (FIG. 1B) A table showing the components and the net charges of BDD as well as its D-configuration (Bdd), neutrally charged (BKD), positively charged (BKK), and pegylated ($PEG_3DD$) counterparts. (FIG. 1C) A synthetic scheme showing radiolabeling of the peptides with $^{89}Zr$ for comparative PK and biodistribution studies. (FIG. 1D) Representative μPET/CT images of BALB/c mice acquired 1, 4, and 24 h after administration of different $^{89}Zr$-radiolabeled peptides (20 μCi, 20 μg, in 100 μL PBS) via tail-vein injections (n=4/group). The whole-body images were acquired with or without emptying the animal's bladders. (FIG. 1E) Bar chart showing the amount of radioactivity in urine samples (20 μL) collected from animals (n=5) at different time intervals after administration of $^{89}Zr$-Bdd. (FIG. 1F) Comparing the renal clearance of the radiolabeled peptides. Plots showing the percentage of injected dose (% ID) in kidneys (per cc) of the animals over time. The percentage of ID/cc was calculated according to the radioactivity measured at the region of interest (ROI) of the acquired PET images. (FIG. 1G) Comparing the pharmacokinetic (PK) profiles of the radiolabeled peptides (n=4/analogue). Blood samples (20 μL) were collected at various time intervals after injection of the peptides or free $^{89}Zr$ to the animals. The results (radioactivity measured in blood samples) were fit into a two-compartmental model for determining the $t_{1/2\alpha}$ (half-life of distribution phase) and $t_{1/2\beta}$ (half-life of elimination phase). The other PK parameters are available in FIG. 7A. (FIG. 1H) End-point biodistribution study of $^{89}Zr$-Bdd. The animals were euthanized at different time intervals (n=4/time point) after administration of the peptide (20 μCi, 20 μg, in 100 μL PBS). The amount of peptide (radioactivity) in the harvested organs were determined. The results (corrected from decay) were expressed as % ID. (Student's t-test; p<0.01, and *p<0.001).

(FIG. 2A) A synthetic scheme of the Cyanine5.5-labeled peptide (Cy-peptide) analogues. (FIG. 2B) Representative merged fluorescence/white light images of SCID mice acquired 1 and 4 h after tail-vein injection of the different Cy-peptide analogues (0.5 nmol, 150 μL) or free Cyanine5.5 (n=4/group). (FIG. 2C) Plots comparing the amount of fluorophore in urine (% of injected dose) based on the measured fluorescence. (Lower panel) Fluorescence image of the urine samples (20 μL) collected from animals 1 h after the peptide or fluorophore administration. (FIG. 2D) Representative ex vivo merged fluorescence/bright light images of the organs harvested from animals 4 h after tail-vein injection of different Cy-peptides (n=4/group). (FIG. 2E) Bar chart comparing peptide distribution in the harvested organs (n=4/group), based on the total fluorescence intensity. (Student's t-test; *p<0.05, p<0.01, and *p<0.001).

(FIG. 3A) Bdd does not trigger any innate immune response. No increase in the inflammatory cytokines concentrations was detected in the plasma of female BALB/c mice (n=3/group) 24 h after i.v. administration of the Bdd peptide (5 mg/kg). LPS was used as a positive control and concentrations of each cytokine was measured by ELISA kit. (FIG. 3B) Cellular uptake of Cyanine5.5-labeled Bdd (Cy-Bdd). Representative fluorescence microscopic images of human UMUC-3 BC cells and murine Renca renal adenocarcinoma cells incubated for 6 and 24 h with Cy-Bdd (0.5 nmol). Dapi (9 μM) and LysoTracker-GFP (1 μM) were used for nuclear (blue) and organelle (green) staining, respectively, and were added to the cells 30 min prior to imaging. Scale bar is 25 m. (FIG. 3C) Comparing the potency of different chemotherapeutics (DM1, GEM, MIT, CIS, and DOX). UMUC-3 and Renca cells were incubated with the drugs at various concentrations for 72 h prior to measuring the cell viability. The dose response curves were plotted and the half maximal inhibitory concentrations ($IC_{50}$ values) of each drug calculated using Graph Pad Prism 6.0 software. (FIG. 3D) Conjugation of DM1 to Bdd. The cleavable linker SPDP was first conjugated to the peptide N-terminal in solid phase. DM1 was then added to the cleaved peptide in a solution mixture of PBS and NMP. (FIG. 3E) Plot showing the percentage of accumulated DM1 released from the DM1-Bdd over time in PBS in the absence and presence of GSH (1 mM). The amount of drug released was quantified using HPLC analysis (absorbance detected at 254 nm). (FIG. 3F) Conjugation of aldox to Bdd. The peptide, supplemented with a N-terminal cysteine, was incubated with aldox in PBS (pH=7.4) for 30 min prior to purification by HPLC in neutral conditions. (FIG. 3G) Plots showing the percentage of the accumulated DOX active metabolite released from aldox-Bdd (100 μM) over time in PBS buffers with different pH values. The amount of drug released was quantified using HPLC analysis (absorbance detected at 480 nm). (FIG. 3H) DM1-Bdd displays a similar cytotoxicity compared to free drug against murine bladder (MB49), human bladder (UMUC-3 and T24, and murine kidney (Renca) cancer cell lines. Plots of relative cell viability against the drug concentration. (FIG. 3I) Aldox-Bdd is more potent than free aldox. Plots of the relative cell viability against the drug concentration.

(FIG. 4A) Bar chart comparing the time when BALB/c mice (n=20/group) needed to void naturally following i.v. or i.t. administration of PBS (80 μL). The bladders were emptied prior to starting the experiment. Each animal was isolated for monitoring the urination pattern. (FIG. 4B) Comparing the nephrotoxicity of DM1-Bdd to other chemotherapeutics. Bar chart showing the concentrations of renal injury biomarkers, NGAL and KIM-1, in urine collected from animals 1, 3, and 7 days after treatment with PBS, DM1 (0.75 mg/kg), DM1-Bdd (0.75 mg/kg of drug content), MIT (0.75 mg/kg), CIS (0.75 and 10 mg/kg), or GEM (0.75 mg/kg) via tail vein injection. (Student's t-test; *p<0.05, p<0.01, and *p<0.001). (FIG. 4C) Immunochemical staining for NGAL and KIM-1 was also performed. Representative microscopic images of kidney sections from BALB/c mice i.v. administered with PBS, DM1 (0.75 mg/kg), DM1-Bdd (0.75 mg/kg of drug content), or CIS (10 mg/kg) as a positive control. The organs were harvested 3 days after the drug treatments and stained with H&E. Black arrows indicate the multifocal degeneration of the tubular epithelium after treatment with CIS. Red and green arrows indicate renal tubular epithelial cells immunoreactive for NGAL and KIM-1, respectively, following CIS treatment. Scale bar is 50 m. (FIG. 4D) Bright field and fluorescence images of UMUC-3/GFP-Luc cells that were stably transduced with a lentivirus carrying both GFP and firefly luciferase genes. Scale bar is 80 m. (FIG. 4E) Orthotopic xenograft model. Representative image of bladders collected from female NSG mice (n=3) 1 week after implantation of UMUC-3/GFP-Luc cells ($4 \times 10^4$ cells/animals). Black arrows indicate the tumors growing in the lamina propia. Scale bar is 500 m. (FIG. 4F) Representative merged bioluminescence/bright field images of the tumor-bearing animals after weekly treatments with i.v. PBS (150 μL), i.v. DM1 (0.75 mg/kg, 150 μL), i.v. DM1-Bdd (0.75 mg/kg of drug content, 150 μL), i.t. MIT (1 mg/mL, 50 μL), i.t. DM1 (0.75 mg/kg, 50 μL), or i.t. DM1-Bdd (0.75 mg/kg, 50 μL) for 3 weeks (n=10/group). Images were acquired every week to monitor and compare tumor growth in each treatment group. (FIG. 4G) Representative pictures of bladders excised from each animal group (additional recruitment of n=3/treatment group) 1 week after completing the treatment cycles. (FIG. 4H) Kaplan-Meier cumulative survival plot of animals administered with different drugs (n=14/group). The significant differences in survival between the animals treated with i.v. DM1-Bdd and the other groups was evaluated using the Mantel-Cox log-rank test and the Benjamini Hochberg adjusted p-values. (FIG. 4I-J) Representative image(s) of bladder sections from the animals in each treatment group (n=3/group). The organs were harvested at the end of the 3-week treatment and then paraffin-embedded, sectioned, and stained with (FIG. 4I) H&E and (FIG. 4J) Ki67 (proliferation marker).

(FIG. 5A) Bright field and fluorescence images of Renca cells that were stably transduced with a lentivirus carrying both GFP and firefly luciferase genes. Scale bar is 80 m. (FIG. 5B) Syngeneic xenograft model. Representative image of the histological analysis of kidneys collected from female BALB/c mice (n=3) 1 week after implantation of murine Renca cells ($4 \times 10^3$ cells/animals) in the renal capsules (black arrow). Scale bar is 1 μmm. (FIG. 5C) Representative merged bioluminescence/bright field images of animals bearing Renca/GFP-Luc tumors after treatment with i.v. PBS (150 μL), i.v. DM1 (0.75 mg/kg, 150 μL), i.v. DM1-Bdd (0.75 mg/kg of drug content, 150 μL), or i.t. DM1 (0.75 mg/kg, 50 μL) weekly for 3 weeks (n=10/group). (FIG. 5D) Representative photos of the kidneys excised from the animals after completion of the treatment cycle (additional n=4/group). Longitudinal comparisons of (FIG. 5E) bioluminescence signals at the region of interest (ROI=kidney), (FIG. 5F) body weight, and (FIG. 5G) survival among animals receiving different treatments (n=14/group). The significant differences in survival between animals treated with i.v. DM1-Bdd and the drugs was evaluated using the Mantel-Cox log-rank test and the Benjamini Hochberg adjusted p-values. (FIG. 5H) Representative kidney sections from animals of each treatment group (additional n=4/group). The sections were stained with H&E. The green, yellow, black, and blue arrows indicate the presence of pigment-laden macrophage, focal mineralization, interstitial fibrosis, and mononuclear cell infiltrates, respectively. Scale bar is 2 mm and 50 m.

(FIG. 6A) Representative microscopic images of blood smears collected from female BALB/c mice after i.v. administration of PBS, DM1 (0.75 mg/kg), DM1-Bdd (0.75 mg/kg of drug content), or CIS (10 mg/kg) as a positive control, weekly for 3 weeks. Black arrows indicate polychromatophilic macrocytes. Scale bar is 10 m. (FIG. 6B) Select hematologic results obtained one week after completing the different treatment courses. (RBC=red blood cells and WBC=white blood cells). (Student's t-test; *p<0.05, p<0.01, and *p<0.001). (FIG. 6C) Comparison of select serum biochemical analytes, including liver enzyme activity (ALP, ALT and AST), muscle enzyme activity (AST and CK), and clearance of nitrogenous waste (BUN/CREA ratio). (ALP=alkaline phosphatase; ALT=alanine aminotransferase; AST=aspartate aminotransferase; CK=creatine kinase; BUN=blood urea nitrogen; CREA=creatine). (FIG. 6D) Histopathological analysis of the major organs (liver, spleen, heart, lungs, and kidneys) from animals administered with the different drug treatments. Black arrows indicate the increased of hepatocyte mitotic activity in liver. Blue arrows show the enhanced hepatic and splenic extramedullary hematopoiesis (EMH). The area in between the white arrows indicates depletions of erythrocytes and EMH elements in the red pulp of the spleen. Red arrows highlight the presence of large and foamy macrophages in the alveoli. Yellow and green arrows indicate flattened renal tubular cells and necrotic sloughed debris of dying cells contained within the lumen, respectively. Scale bar is 30 m.

(FIG. 7A) Table comparing the pharmacokinetic parameters of the radiolabeled peptides (n=4/analogue). Blood samples (20 μL) were collected at various time intervals after tail vein injections of the peptides or free $^{89}$Zr (20 μCi, 20 μg, in 100 μL PBS) to the animals. The results (radioactivity measured in blood samples) were fit into a two-compartmental model for determining the PK parameters. ($k_{10}$=elimination rate constant; $k_{12}$ and $k_{21}$=transfer rate constant; $t_{1/2\alpha}$=half-life of distribution phase; $t_{1/2\beta}$=half-life of elimination phase; $C_0$=threshold of drug concentration for elimination; $V_d$=apparent volume of distribution; CL=total clearance rate; AUC=area under the curve; MRT=mean residence time; and $V_{ss}$=steady state volume of distribution). (FIG. 7B) End-point biodistribution study of $^{89}$Zr-Bdd. The animals were euthanized at different time intervals (n=4/time point) after administration with the peptide. The amount of peptide (radioactivity) in the harvested organs were determined. The results (corrected from decay) were expressed as % of injected dose per gram of tissue (% ID/g). (Student's t-test; *p<0.05, and ***p<0.001).

(FIG. 8A) Body weight changes in NSG mice bearing bladder tumors and treated with i.v. PBS (150 μL), i.v. DM1 (0.75 mg/kg, 150 μL), i.v. DM1-Bdd (0.75 mg/kg of drug content, 150 μL), i.t. MIT (1 mg/mL, 50 μL), i.t. DM1 (0.75 mg/kg, 50 μL), or i.t. DM1-Bdd (0.75 mg/kg, 50 μL), weekly for 3 weeks. (FIG. 8B) Comparison of the bioluminescence signal at the region of interest (ROI=bladder) among the different drugs. (FIG. 8C) Representative images of bladders excised from 3 animals administered with the different drug treatments. (FIGS. 8D-E) Plots comparing the volume (FIG. 8D) and weight (FIG. 8E) of the bladders. (Student's t-test; *p<0.05, p<0.01, and *p<0.001). (FIG. 8F) Representative images of bladder sections from animals in each treatment group (n=3/group). The organs were harvested at the end of the 3-week treatment and then paraffin-embedded, sectioned, and stained with an anti-GFP antibody to identify GFP-expressing tumor cells. (FIG. 8G) Representative images of the bladder sections from the 3 animals which lacked gross and histologic evidence of tumors after i.v. DM1-Bdd treatment. The animals were sacrificed 210 days after tumor implantation and the organs were harvested, paraffin-embedded, sectioned, and stained with H&E, Ki67 (proliferation marker), and an anti-GFP antibody.

(FIG. 9A) Representative merged bioluminescence/bright field images of NSG mice bearing orthotopically implanted UMUC-3/GFP-Luc bladder tumors after treatment with i.v. PBS (150 μL), i.v. DOX (5 mg/kg, 150 μL), i.v. aldox-Bdd (5 mg/kg of drug content, 150 μL), or i.t. DOX (5 mg/kg, 50 μL), weekly for 3 weeks (n=10/group). Images were acquired every week to monitor and compare the tumor growth in each treatment group. (FIG. 9B) Comparison of the bioluminescence signal at the region of interest (ROI=bladder) among the different treatment groups. (FIG. 9C) Kaplan-Meier cumulative survival plot of animals administered the different drugs (n=10/group). The significant differences in survival between the animals treated with i.v. aldox-Bdd and the other groups was evaluated using the Mantel-Cox log-rank test and the Benjamini Hochberg adjusted p-values. (FIG. 9D) Body weight changes in NSG mice bearing bladder tumors and treated with PBS, i.v. DOX, i.v. aldox-Bdd, or i.t. DOX weekly for 3 weeks. (FIG. 9E) Representative picture of a mouse treated with i.v. DOX (5 mg/kg) after administration of only 2 doses of drug.

FIG. 10. Extended results of the complete blood count analysis. Table showing hematologic results after i.v. administration in BALB/c mice of PBS, DM1 (0.75 mg/kg), DM1-Bdd (0.75 mg/kg of drug content), or CIS (10 mg/kg) used as a positive control, weekly for 3 weeks. (RBC=red blood cells; HGB=hemoglobin; HCT=hematocrit; MCV=mean corpuscular volume; MCH=mean corpuscular hemoglobin; MCHC=mean corpuscular hemoglobin concentration; RDW=red blood cell distribution width; RET=reticulocyte; PLT=platelet; PDW=platelet distribution width; MPV=mean platelet volume; WBC=white blood cell; NEUT=neutrophil; LYMPH=lymphocyte; MONO=monocyte; EO=eosinophil; and BASO=basophil).

FIG. 11. Extended results of the serum biochemical analysis. Table showing results of all biochemical analytes measured after i.v. administration in BALB/c mice of PBS, DM1 (0.75 mg/kg), DM1-Bdd (0.75 mg/kg of drug content), or CIS (10 mg/kg) as a positive control, weekly for 3 weeks. (BUN=blood urea nitrogen; CREA=creatinine; ALP=alkaline phosphatase; ALT=alanine aminotransferase; AST=aspartate aminotransferase; GGT=gamma-glutamyl transferase; BIL=bilirubin; TP=total protein; ALB=albumin; GLOB=globulin; A/G=albumin/globulin; P=phosphate; Ca=calcium; GLU=glucose; CHOL=cholesterol; TRIG=triglyceride; CK=creatine kinase; TCO2=total carbon dioxide; Na=sodium; K=potassium; and CL=chloride).

DETAILED DESCRIPTION OF THE INVENTION

Different approaches have been proposed to improve intravesical chemotherapy (ITC) treatment. To prolong treatment duration, a thermal-sensitive hydrogel, UGN-102, was designed to convert into a semi-solid drug depot inside the bladder and slowly release mitomycin (MIT). A gemcitabine (GEM)-containing semipermeable silicon tube, GemRis, which functions as an osmotic pump, has also been developed to control the release of GEM. Other treatments are currently being tested in clinical in trials for patients who do not respond to BCG. Oportuzumab Monatox is an antibody-protein conjugate that targets tumor cells expressing EpCAM. Adstiladrin is a nonreplicating adenovirus vector that encodes the human IFNα-2b gene. The resulting IFNα-2b proteins, synthesized and expressed in a large quantity, displayed an antitumor activity through inhibition of angiogenesis and induction of apoptosis in human bladder cancer cells. However, all the aforementioned approaches are invasive, requiring catherization and/or surgical procedures. Alternatively, renal-clearable nanoparticles can be used as drug carriers. However, they are known to be non-specifically captured by the reticuloendothelial system, leading to a high off-target accumulation in the liver.

Advances in phage display have led to the discovery of many bioactive peptides that target the urinary system (URS). For example, a galectin-3 targeting peptide, G3-C12, has been used for delivering captopril, an angiotensin-converting enzyme inhibitor. Another peptide, (KKEEE)$_3$K, was used to carry ciprofloxacin. These peptides were pharmacologically active. They primarily targeted the kidneys via binding to cell-surface receptors and have prolonged the post-delivery local retention. They have not been applied for BC treatment. In fact, without chemical modifications, a peptide is not a good drug candidate or carrier. It displays unfavorable pharmacokinetics (PK), is rapidly degraded by protease enzymes, and can be eliminated by renal filtration.

Figures 1A, 1B:
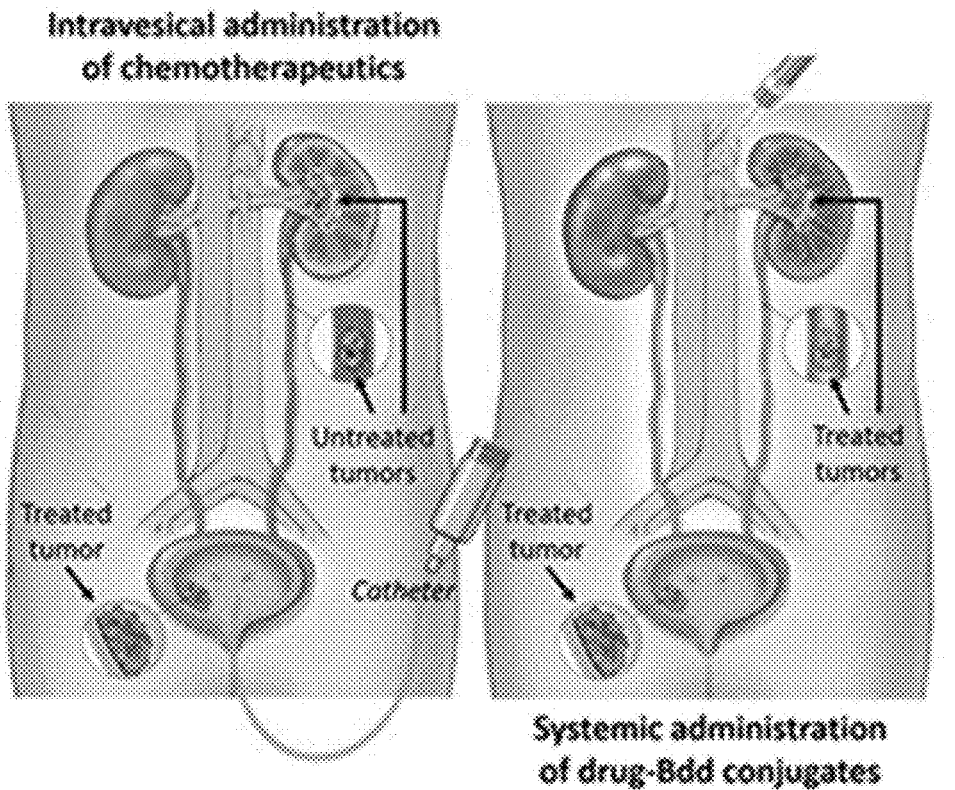
FIGS. 1A-H Bdd shows remarkable urinary disposing properties.

The present invention exploits a peptide's rapid renal clearance for disposing treatments to the URS. In certain embodiments, the present disclosure provides a small (e.g., 12-amino acid), negatively charged, peptide (e.g., Bdd) that can bypass the recticuloendothelial system and other organs and is preferentially (e.g., exclusively) excreted into the urine with minimal reabsorption. In certain embodiments, the present disclosure provides an alternative to ITC, for minimizing off-target accumulation in other organs, promoting drug delivery to the URS, and prolonging bladder retention time, to offer a comprehensive and more effective treatment of BC (FIG. 1a).

The present disclosure relates to a systemically administered peptide delivery platform that biodistributes to the kidney or urinary tract. In certain embodiments an active moiety is linked to the peptide delivery platform. The disclosure further relates to methods of treating a disease of the kidney or urinary tract in a subject in need thereof. In some embodiments, the disease is an acute renal disease. In some embodiments, the disease is a chronic renal disease.

In certain embodiments, the peptide delivery platform comprises a negatively charged peptide that can temporary accumulate in kidneys, with no off-target delivery to other organs. Because the peptide is eliminated gradually in urine, it is useful as a drug delivery platform to provide a continuous drug flow for treatment of diseases of the kidney or urinary tract, such as BC. The peptide delivers systemically administered drugs to the urinary system while prolonging bladder retention time, providing a more effective treatment.

In certain aspects, the peptide has multiple negative charges that can promote rapid renal clearance. Drug delivery to the bladder via renal clearance is thus a continuous event. Compared to drug administration via catheterization, the peptide can enhance the therapy's infiltration of the entire urinary system with a longer dwell time in the bladder, resulting in a more effective treatment that is non-invasive. In certain aspects, the peptide is used as a drug delivery system for BC treatment, using mertansine (DM1), a highly cytotoxic microtubule inhibitor. DM1 is too toxic to be used alone but was approved as a pharmacophore in antibody-drug conjugates, such as T-DM1. In certain aspects, the peptide is used to deliver DM1 to treat BC, as well as other cancers of the urinary tract.

In certain aspects, the peptide is used as a drug delivery system for treatment of a urinary tract infection, for example, with an antibiotic. In certain aspects, the peptide is used as a drug delivery system for treatment of kidney stones. In certain aspects, the peptide is used as a drug delivery system for treatment of over active bladder. In certain aspects, the peptide is used as a drug delivery system for treatment of urinary incontinence. In certain aspects, the peptide is used as a drug delivery system for treatment of interstitial cystitis. In certain aspects, the peptide is used to deliver an imaging agent to the bladder.

In certain aspects, the peptide is water soluble, biologically inert, and non-immunogenic. After IV injection, the peptide can be exclusively eliminated via renal clearance with a minimal accumulation in other organs, including heart, liver, and spleen.

In certain aspects, the present disclosure provides a compound represented by formula (I):

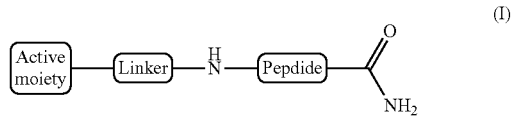

or a pharmaceutically acceptable salt thereof, wherein the peptide is a peptide targeted for renal clearance.

In certain embodiments, the peptide targeted for renal clearance comprises a sequence:

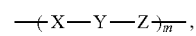

wherein one of X, Y and Z is a j-amino acid residue, two of X, Y and Z are independently α-amino acid residues that each have at least one side chain that comprises a carboxylic acid group, each α-amino acid residue may independently be of D or L stereochemistry and m is from 2 to 10.

In certain embodiments, the peptide has a zeta potential of from about −30 mV to about +20 mV at physiological pH. In certain embodiments, the peptide has a zeta potential of from about −20 mV to about 0 mV at physiological pH. In certain embodiments, the peptide has a zeta potential of from about −5 mV to about 0 mV at physiological pH.

In certain embodiments, the linker comprises one or more groups selected from: amide, imide, thiourea, thioether, disulfide, alkyl, aryl, polyether, hydrazone, ester, carbonate, ketal and silyl ether. In certain embodiments, the active moiety is a therapeutic agent or an imaging agent.

In certain embodiments, the peptide targeted for renal clearance comprises a sequence:

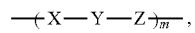

wherein one of X, Y and Z is a j-amino acid residue two of X, Y and Z are independently α-amino acid residues that each have at least one side chain that comprises a carboxylic acid group, each α-amino acid residue may independently be of D or L stereochemistry, m is from 2 to 10, the linker comprises one or more groups selected from: amide, imide, thiourea, thioether, disulfide, alkyl, aryl, polyether, hydrazone, ester, carbonate, ketal and silyl ether; and the active moiety is a therapeutic agent or an imaging agent.

In certain embodiments, the compound is represented by formula (IA):

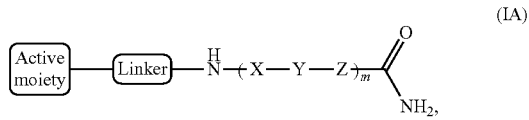

or a pharmaceutically acceptable salt thereof.

In certain embodiments, the j-amino acid residue does not comprise an ionizable side chain. In certain embodiments, the j-amino acid residue is a β-alanine residue. In certain embodiments, X is a β-alanine residue. In certain embodiments, each α-amino acid residue is independently selected from an aspartic acid residue and a glutamic acid residue. In certain embodiments, at least one α-amino acid residue is an unnatural amino acid residue. In certain embodiments, the unnatural α-amino acid residue has at least two side chain carboxylic acid groups. In certain embodiments, the unnatural α-amino acid residue is selected from a 2-aminoethane-1,1,2-tricarboxylic acid residue and a 2-aminopropane-1,2,3-tricarboxylic acid residue. In certain embodiments, each Y and Z are aspartic acid residues. In certain embodiments, each Y and Z are D-aspartic acid residues. In certain embodiments, X, Y and Z are each independently selected from a β-alanine residue, an aspartic acid residue and a glutamic acid residue. In certain embodiments, m is 4.

In certain embodiments, the linker comprises a group selected from:

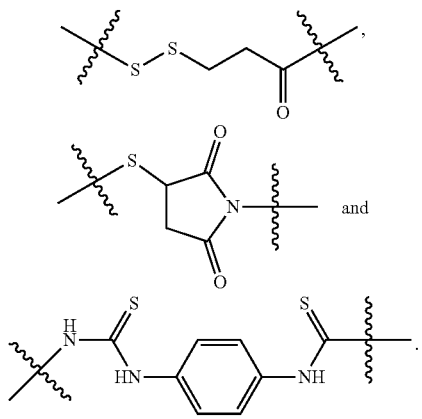

In certain embodiments, the linker comprises a group derived from N-succinimidyl 3-(2-pyridyldithio)propionate or succinimidyl 4-(N-maleimidomethyl)cyclohexane-1-carboxylate.

In certain embodiments, the active moiety is a therapeutic agent. In certain embodiments, the therapeutic agent is selected from an anticancer agent, an antibiotic, an agent that treats overactive bladder, an agent that treats urinary incontinence, an agent that treats interstitial cystitis and an agent that treats kidney stones. In certain embodiments, the therapeutic agent is selected from 13-cis-Retinoic Acid, 2-Chlorodeoxyadenosine, 5-Azacitidine. 5-Fluorouracil, 6-Mercaptopurine, 6-Thioguanine, actinomycin-D, adriamycin, aldesleukin, alemtuzurnab, alitretinoin, all-transretinoic acid, alpha interferon, altretamine, amethopterin, amifostine, anagrelide, anastrozole, arabinosylcytosine, arsenic trioxide, amsacrine, aminocarmptothecin, aminoglutethimide, asparaginase, azacytidine, bacillus calmetteguerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, doceaxtel, doxorubicin, doxil, aldoxorubicin, doxifluridine, edrecolomab, eniluracil, epirubicin, epoctin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemituzumnab ozogamicin, goserelin, granulocyte-colony stimulating factor, granulocyte macrophage-colony stimulating factor, hexamethylmelamine, hydrocortisone hydroxyurea, ibritumomab, ibritmomab tiuxetan, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorctharmine, megestrol melphalan, mercaptopurine, mertansine, mesna, methotrexate, methylprednisolone, mioiycin C, mitotane, mioxantrone, nelarabine, nilutamide, octrcotide, oprelvekin, oxaliplatin, paclitaxel, pamidronate, pemetrexed, panitumumab, PEG Interferon, pegaspargase, pegfilgrastin, PEG-L-asparaginase, pentostatin, plicamycin, prednisolone, prednisone, procarbazine, raloxifecn, rituximab, romiplostim, ralitrexed, sapacitabine, sargramostim, satraplatin, sorafenib, sunitinib, serustine, streptozoein, tamoxifen, tegafur, tegafur-uracil, temsirolimus, tcmozolamidc, teniposide, thalidornide, thioguanine, thiotepa, topotecan, torcmifene, tositumomab, trastuzumab, trastuzumab emtansine, tretinoin, trinitrexate, alubicin, vincristine, vinblastine, vindcsine, vinorelbine, vorinostat, and zoledronic acid.

In certain embodiments, the therapeutic agent is an anticancer agent. In certain embodiments, the anticancer agent is selected from mertansine, doxorubicin, dasatinib, cisplatin, mitomycin, gemcitabine and paclitaxel.

In certain embodiments, X is a β-alanine residue, and Y and Z are D-aspartic acid residues. In certain embodiments, X is a β-alanine residue, Y and Z are D-aspartic acid residues and m is 4. In certain embodiments, X is a β-alanine residue, Y and Z are D-aspartic acid residues, m is 4, the linker comprises a disulfide group; and the active moiety is mertansine.

In certain embodiments, the compound is:

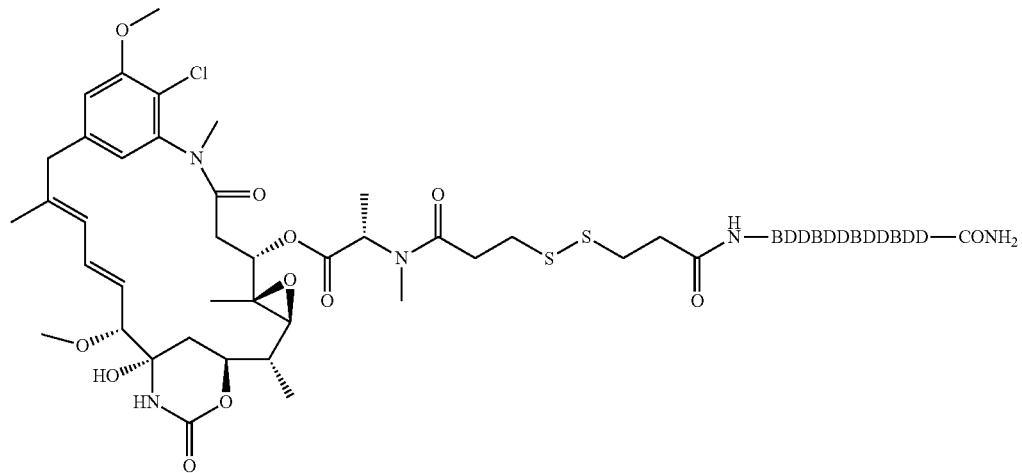

or a pharmaceutically acceptable salt thereof, wherein B is a β-alanine residue and D is an aspartic acid residue of D or L configuration.

In certain embodiments, the compound is:

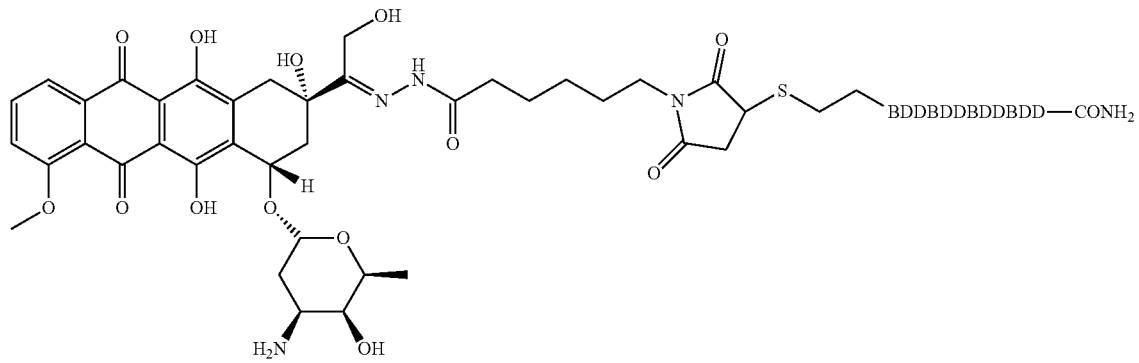

or a pharmaceutically acceptable salt thereof, wherein B is a β-alanine residue and D is an aspartic acid residue of D or L configuration.

In certain embodiments, the present disclosure provides a pharmaceutical composition comprising a compound of the invention. In certain embodiments, the composition is formulated for intravenous administration.

In certain embodiments, the present disclosure provides a method of treating cancer, a urinary tract infection, overactive bladder, urinary incontinence, interstitial cystitis or kidney stones comprising administering to a patient in need thereof a compound or composition of the invention. In certain embodiments, the present disclosure provides a method of treating cancer, comprising administering to a patient in need thereof a compound or composition of the invention. In certain embodiments, the cancer is a cancer of the kidney or urinary tract. In certain embodiments, the cancer is bladder cancer. In certain embodiments, the bladder cancer is non-muscle invasive bladder cancer. In certain embodiments, the bladder cancer is urothelial carcinoma. In certain embodiments, the compound is administered intravenously.

Pharmaceutical Compositions

The compositions and methods of the present disclosure may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the disclosure and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-2microemulsifying drug delivery system. The pharmaceutical composition (preparation) also can be a liposome or other polymer matrix, which can have incorporated therein, for example, a compound of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (or preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation.

In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the disclosure, with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compositions or compounds may also be administered as a bolus, electuary or paste.

To prepare solid dosage forms for oral administration (capsules including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this disclosure, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with a compound of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the disclosure may be used alone or conjointly administered with another type of therapeutic agent.

The present disclosure includes the use of pharmaceutically acceptable salts of compounds of the disclosure in the compositions and methods of the present disclosure. In certain embodiments, contemplated salts of the disclosure include, but are not limited to, alkyl, dialkyl, trialkyl or tetra-alkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the disclosure include, but are not limited to, Na, Ca, K, Mg, Zn or other metal salts. In certain embodiments, contemplated salts of the disclosure include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present disclosure can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—CH$_2$—O-alkyl, —OP(O)(O-alkyl)$_2$ or —CH$_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to C$_1$-C$_{10}$ straight-chain alkyl groups or C$_1$-C$_{10}$ branched-chain alkyl groups. Preferably, the "alkyl" group refers to C$_1$-C$_6$ straight-chain alkyl groups or C$_1$-C$_6$ branched-chain alkyl groups. Most preferably, the "alkyl" group refers to C$_1$-C$_4$ straight-chain alkyl groups or C$_1$-C$_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., C$_{1-30}$ for straight chains, C$_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "C$_{x-y}$" or "C$_x$-C$_y$", when used in conjunction with a chemical moiety, such as, acyl, acyloxy, alkyl, alkenyl, alkynyl, or alkoxy is meant to include groups that contain from x to y carbons in the chain. C$_0$alkyl indicates a hydrogen where the group is in a terminal position, a bond if internal. A C$_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS-.

The term "amide", as used herein, refers to a group

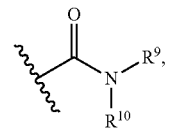

wherein R$^9$ and R$^{10}$ each independently represent a hydrogen or hydrocarbyl group, or R$^9$ and R$^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

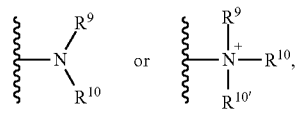

wherein R$^9$, R$^{10}$, and R$^{10'}$ each independently represent a hydrogen or a hydrocarbyl group, or R$^9$ and R$^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

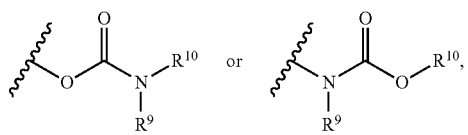

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group —$OCO_2$—.

The term "carboxy", as used herein, refers to a group represented by the formula —$CO_2H$.

The term "ester", as used herein, refers to a group —$C(O)OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

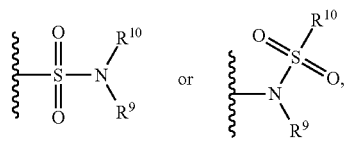

wherein $R^9$ and $R^{10}$ independently represents hydrogen or hydrocarbyl.

The term "sulfoxide" is art-recognized and refers to the group-S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

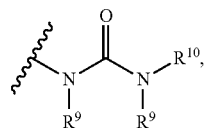

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "LogS" or "logS" as used herein is used in the art to quantify the aqueous solubility of a compound. The aqueous solubility of a compound significantly affects its absorption and distribution characteristics. A low solubility often goes along with a poor absorption. LogS value is a unit stripped logarithm (base 10) of the solubility measured in mol/liter.

EXAMPLES

The disclosure now being generally described, it will be more readily understood by reference to the following examples which are included merely for purposes of illustration of certain aspects and embodiments of the present disclosure, and are not intended to limit the disclosure.

Materials and Methods

Chemicals and Supplies—2(1H-benzotriazole-1-yl)-1,1,3,3-tetramethyluroniumhexafluorophosphate (HBTU) and the N-hydroxybenzotriazole (HOBt) were purchased from Vivitide (Gardner, MA). All protected amino acids, rink amide MBHA resin, and N-methylmorpholine (NMM) were supplied by Gyros Protein Technologies (Tucson, AZ). Polyethylene glycol ($PEG_3$) was obtained from Creative PEG-Works (Durham, NC). Trifluoroacetic acid (TFA), piperidine, thioanisole, anisole, 1,2-ethanedithiole, methyl-tert-butyl ether, N,N-diisopropylethylamine (DIPEA), dimethylformamide (DMF), acetonitrile (ACN), N-methyl-2-pyrrolidone (NMP), sodium carbonate, Sephadex G25, L-glutathione reduced (GSH), lipopolysaccharide (LPS), and cis-dichlorodiammine platinum (II) (cisplatin) were purchased from Sigma Aldrich (Saint-Louis, MO). Succinimidyl 3-(2-pyridyldithio)propionate (SPDP) was supplied by Invitrogen (Carlsbad, CA). p-SNC-deferoxamine (DFO) was from Macrocyclics Inc. (Plato, TX). N2'-deacetyl-N2'-(3-mercapto-1-oxopropyl)-maytansine (DM1) and aldoxorubicin HCl (aldox) were from MedKoo Biosciences (Morrisville, NC). Doxorubicin (DOX) and gemcitabine (GEM) were obtained from LC Laboratories (Woburn, MA). Mitomycin (MIT) was supplied by Selleckchem (Houston, TX). Cyanine5.5 NHS ester was purchased from Lumiprobe Corporation (Hallandale Beach, FL) and luciferin was from Caliper LifeScience (Hopkinton, MA).

Peptide synthesis—All peptides were synthesized on a solid-phase peptide synthesizer (PS3, Gyros Protein Technologies, Tucson, AZ) using the N-α-Fmoc methodology on Rink amide resin, as previously described. The side-chain protected amino acids (0.4 mmol) were attached to the resin (385 mg, 0.1 mmol) by stepwise elongation using NMM as a base, HBTU/HOBt as coupling reagents, and piperidine (20% in DMF v/v) as a deprotecting agent. A β-alanine was incorporated at the peptide N-terminal as a spacer for further conjugation of the desired moieties, including fluorophore (Cyanine5.5), chelator (DFO), or linker (SPDP) prior to peptide cleavage.

Immunogenicity assay—Female BALB/c mice were treated with a single dose of Bdd or LPS (5 mg/kg) via tail-vein injection (n=3/group). Mice administered with PBS were used as a negative control. Blood samples were collected 4 h later via retro-orbital sinus puncture technique, and the concentration of the innate immune and inflammatory cytokines IL1β, IL2, IL6, IL10, TNF-α, and INF-γ in plasma was measured with commercial sandwich enzyme-linked immunosorbent assay kits. ELISA assays were performed according to the manufacturer's instructions (Invitrogen, Carlsbad, CA).

Methods to incorporate different functionalities to peptide—Cyanine5.5 NHS ester (50 mg, 1.4 eq) in DMF (4 mL), DFO (25 mg, 1 eq) in DMSO (4 mL), or SPDP (25 mg, 1 eq) in NMP (4 mL), were added to the resin (0.05 mmoL, 1 eq) and allowed to react overnight at room temperature. For fluorophore and chelator conjugation, the reactions were performed in presence of an organic base (DIPEA, 1 mL). The peptides were then removed from the resin using a cleaving cocktail (5 mL) containing TFA/thioanisole/1,2-ethandithiol/anisole (90:5:3:2) for 4 h and precipitated in methyl-tert-butyl ether. The resulting peptides (Cy-peptide, DFO-peptide, and SPDP-peptide) were purified to >98% purity using reverse-phase high performance liquid chromatography (rp-HPLC, Agilent, Santa Clara, CA) and were characterized by MALDI-TOF analysis (Tufts Medical School, Boston, MA) to confirm their molecular weights.

Synthesis of cleavable drug-peptide conjugate—DM1 (1 mg, 1 eq) was added to SPDP-peptide (10 mg, 3 eq) in a cosolvent of NMP (100 µL) and phosphate-buffered saline (PBS; 10 mM, pH 7, 100 µL), and allowed to react for 2 days at room temperature. The DM1-peptide was then purified by rp-HPLC. To conjugate aldox, a thiol-reactive side (cysteine) was introduced at the peptide N-terminal. Aldox (2 mg, 1 eq) was added to the peptide (10 mg, 3 eq) in PBS (10 nM, 1 mL, pH 7.4), and allowed to react for 30 minutes. The drug-peptide obtained was pH-sensitive and thereby was purified by rp-HPLC in neutral conditions (mobile phase A: PBS, mobile phase B: 90% ACN in PBS). Size exclusion chromatography (TipTop C-18 column) was used to remove the salt content. All the final drug-peptide conjugates were characterized using MALDI-TOF analysis and were quantified with UV absorbance, according to the pre-determined extinction coefficient of DM1 (e=3,700 cm$^{-1}$ M$^{-1}$) or aldox (e=13,000 cm$^{-1}$ M$^{-1}$) in 5% (v/v) PBS in methanol.

Radiochemistry—$^{89}$Zirconium ($^{89}$Zr) was supplied by 3DImaging LLC (Little Rock, AR). The $^{89}$Zr-oxalate (500 μCi) was first neutralized with an equivalent volume of sodium carbonate solution (2 M), and then added to the DFO-peptides (0.2 mg, 250 μL). After incubation for 1.5 h at room temperature, the radiolabeled peptides ($^{89}$Zr-peptides) were purified by size exclusion chromatography using Sephadex G-25 gel to remove the free zirconium.

Pharmacokinetic study—BALB/c mice (Jackson Laboratory, Bar Harbor, ME) were administered with $^{89}$Zr-peptide or free $^{89}$Zr (20 μCi, 100 μL) via tail-vein injections (n=4/condition). Blood samples (20 μL) were collected at various time intervals, using retro-orbital sinus puncture technique. The radioactivities were measured on Wallac Wizard 2 gamma counter (Perkin-Elmer, Waltham, MA). The pharmacokinetic models and parameters of $^{89}$Zr-peptides and free $^{89}$Zr, including the serum half-life and the plasma clearance, were estimated by fitting the data for compartmental model selection using PKSolver 2.0 software.

μPET/CT imaging and biodistribution study—BALB/c mice were intravenously injected with different $^{89}$Zr-peptide analogues (20 μCi, 100 μL). PET/CT imaging was performed in animals with and without urine collection prior to the first imaging (n=4/analogue/condition). Whole-body images were acquired 1, 4, and 24 h after injection, using Inveon PET/CT scanner (Siemens Medical Solutions, Malvern, PA). PET/CT maximum energy projections were processed using Amide v1.0.4 and Inveon Research Workplace software. The radioactivities at different region of interest (ROI) were determined. For end-point biodistribution studies, the mice were euthanized 0.17, 1, 2, 5, and 7 days after treatment with $^{89}$Zr-peptides (n=3/peptide analogue/time point). The radioactivities of the harvested organs were measured using the Wallac Wizard 2 gamma counter. The results were corrected from radioactive decay, and were expressed as a percentage of the injected dose (% ID) or percentage of injected dose per gram of tissue (% ID/g).

Fluorescence imaging—Female SHO mice (Charles River Laboratories, Wilmington, MA) were administered with free Cyanine5.5 or $C_y$-peptide analogues (0.5 nmol of Cyanine5.5 content measured by UV absorbance at 680 nm) in a PBS (150 μL) via tail-vein injections (n=4/group). Real-time fluorescence imaging was performed using In vivo Xtreme imaging system (Bruker, Billerica, MA). Whole body fluorescence images were acquired 1 and 4 h post injection using the appropriate excitation (670 nm) and emission (750 nm) filters. The animals were then euthanized. The organs were excised to perform ex vivo fluorescence imaging. Imaging was also performed on urine samples (50 μL) collected from separate animals 1 h after i.v. injection of free dye or $C_y$-peptide analogues (n=4/treatment). Bruker MI software was used to process the fluorescence/bright light images and measure the fluorescence intensity in different ROIs. All the data were corrected to eliminate the organ or fluid auto-fluorescence.

Cell lines—MB49 was supplied by EMD Millipore Corporation (Temecula, CA). UMUC-3, T24, and Renca were obtained from ATCC (Manassas, VA). Each cell line was cultured according to the company's instructions. *Mycoplasma* tests (Lonza, Basel, Switzerland) were performed periodically to ensure that there was no contamination. Both UMUC-3 and Renca cell lines were further transduced with GlowCell 16 FLuc-F2A-GFP lentivirus (Biosettia, San Diego, CA) carrying both firefly luciferase and green fluorescent protein (GFP) genes. Briefly, the cells were seeded in 6-well plates (0.25×10$^6$ cells/well) and incubated for 3 days with the virus (2×107 IU/well) in the presence of polybrene (10 μg/mL). To ensure more than 95% of cell purity, the cell lines were analyzed and sorted for GFP expression using flow cytometry. The successful transduction was further confirmed by imaging, using EVOS FL Auto Fluorescence microscope (Life Technology, Carlsbad, CA).

Cell viability and cytotoxicity assay—Cancer cells (3×10$^3$/well) were seeded on a flat bottom 96-well plate overnight. Different concentrations of DM1, gemcitabine (GEM), mitomycin (MIT), cisplatin (CIS), doxorubicin (DOX), aldoxorubicin (aldox), or drug-loaded peptides (DM1-peptide and aldox-peptide), were then added to the cells for 72 h and then washed 2 times with PBS (400 μL). CellTiter Glo reagent (Promega, Madison, WI) was added in each well (50 μL). The luminescence generated was recorded using a microplate reader (Tecan US Inc., Morrisville, NC). The dose response curves were plotted, and the half maximal inhibitory concentrations (IC$_{50}$ values) were calculated using Graph Pad Prism 6.0 software.

In vitro drug release study—DM1-peptide conjugates (10 μM of drug content) were incubated in the presence of the reducing agent GSH (1 mM) in PBS buffer (800 μL). At different time intervals (0, 2, 4, 6, 8, 12, 24, and 48 h), a small amount of solution (100 μL) was taken out for HPLC analysis using C18 analytical column. The amount of DM1 active metabolites released over time was measured (absorbance detected at 254 nm) and then quantified. The experiment was performed independently in triplicate. A similar experiment was performed to quantify the release of aldox. Aldox-peptide conjugates (100 μM of drug content) were incubated in PBS buffer (800 μL) with different pH (7.4 and 5.5) in a glass vial coated with silica to avoid non-specific adsorption on the reaction vessel surfaces. The amount of drug released over time was then measured as described above (absorbance detected at 480 nm). For accurate quantification, all the results were normalized compared to a DOX control incubated in similar conditions.

Animal care—All animals used for this project were housed in a pathogen-free barrier room, maintained at a controlled temperature (72±2° F.) with daily 12 h cycle of light and dark. All the procedures conducted on mice were approved by the Weill Cornell Medical Center Institutional Animal Care and Use Committee (protocol #2019-0003), and were consistent with the recommendations of the American Veterinary Medical Association and the National Institutes of Health Guide for the Care and Use of Laboratory Animals. The mice were allowed to acclimate for at least 7 days before performing any experiment. Immunocompromised NSG mice are susceptible to infection. Thus, the animals were fed with diet containing sulfatrim antibiotic (Envigo, Indianapolis, IN). Animals used for fluorescence imaging were fed with AING93 non-fluorescence diet (Envigo, Indianapolis, IN).

Therapeutic efficacy of drug-Bdd conjugates for treating BC—Animals were orthotopically implanted with tumors as previously described. Briefly, the urine of 7- to 9-week-old female NSG mice (Jackson Laboratory, Bar Harbor, ME) was remove through a sterile 24 G pediatric venous catheter (Dublin, Ireland). A trypsin solution (0.125%, 80 µL) was then delivered into the bladder. Subsequently, UMUC-3/GFP-Luc cells (4×10$^4$ cells) in culture media (50 IL) were transferred into the bladders and allowed for seeding. Tumor progression was monitored by bioluminescence imaging. Luciferin (3 mg) in PBS (100 µL) was given to the animals (via intraperitoneal injection) 15 min prior to performing imaging. Once tumor progression was confirmed in bladders (based on bioluminescence signal), the animals were randomly assigned for weekly treatment with PBS, DM1, or DM1-Bdd (0.75 mg/kg of drug content) in saline (150 µL) via tail-vein injection for 3 weeks (n=14/group). Separate groups of animals were assigned for intravesical DM1, DM1-Bdd (0.75 mg/kg of drug content), or MIT (1 mg/mL) in saline (50 µL) treatments (n=14/group). The therapeutic efficacy was evaluated based on tumor growth inhibition (bioluminescence imaging) and long-term survival. Additional mice were recruited for histopathological analysis (n=4/group). These animals were immediately euthanized 1 week after the completion of the treatment schedule. The bladders were harvested and preserved in neutral buffered formalin (10%). The same experimental conditions were used for comparing the treatment outcomes among animals treated with PBS, aldox, or aldox-Bdd via tail-vein injection or intravesical administration (5 mg/kg of drug content).

Evaluation of DM1-Bdd for Kidney cancer treatment—Renca/GFP-Luc cells (4×10$^3$ cells) in PBS (3 µL) were orthotopically implanted into the kidney capsules of 7- to 9-week-old female BALB/c mice (Jackson Laboratory, Bar Harbor, ME) as previously described. The tumor progression was confirmed by bioluminescence imaging. The animals were randomly assigned into 4 groups for weekly treatment with PBS, DM1, or DM1-Bdd (0.75 mg/kg of drug content) through tail-vein injection, or DM1-Bdd (0.75 mg/kg of drug content) through intravesical administration (n=14/treatment). The animals were monitored for tumor growth inhibition and survival as described above. Additional mice were used for histopathological analysis (n=4/group).

Histologic analysis—The tissue samples were fixed in formalin, dehydrated with ethanol, and embedded in paraffin. The tissue sections (5 µm) were stained with hematoxylin and eosin Y (H&E). For immunohistochemistry, the bladder sections were deparaffined and then rehydrated before incubation with anti-Ki67 or anti-GFP antibodies (Abcam, Cambridge, UK) overnight. Slides were then counterstained with Hematoxylin. High resolution images were acquired using Aperio 9 Digital Pathology slide scanner (Leica Biosystems, Weltzar, Germany).

Necropsy—Seven- to 9-week-old female BALB/c mice (n=4/group) were treated weekly with PBS, DM1, DM1-peptide (0.75 mg/kg of drug content), or cisplatin (10 mg/kg) via tail-vein injection (150 µL). At the end of a 3-week treatment, mice were euthanized. The organs/tissues were harvested, fixed in 10% neutral buffered formalin for 2 days. Bones were decalcified in a formic acid solution (Surgipath Decalcifier I; Leica Biosystems, Weltzar, Germany). The samples were then embedded in paraffin, sectioned (5 µm), and stained with H&E for examination by an ACVP board certified anatomic pathologist.

Nephrotoxicity studies—PBS, DM1, DM1-peptide, MIT, GEM, CIS (0.75 mg/kg of drug content), or a high dose of CIS (10 mg/kg), were administered to BALB/c mice via the tail veins (n=3/group). The level of the acute renal injury biomarkers, neutrophil gelatinase-associated lipocalin (NGAL) and kidney injury molecule-1 (KIM-1) in the urine samples, were measured using ELISA assays according to the manufacturer's instructions (R&D Systems, Minneapolis, MN). The complementary histopathological analyses were performed on the kidneys of animals treated with PBS, DM1, DM1-Bdd, (0.75 mg/kg of drug content), or a high dose of CIS (10 mg/kg). All the animals (n=3/group) were euthanized at the end of the treatment and the kidneys were collected and fixed in 10% neutral buffered formalin. The tissues were then processed, embedded in paraffin, sectioned, and stained with H&E. Immunohistochemistry (IHC) for kidney injury (NGAL and KIM-1) was also performed.

Hematology and biochemistry—Blood samples were collected via cardiac puncture. A complete blood count, including red blood cell, white blood cell, reticulocyte and platelet counts, with an automated differential leukocyte count, was performed using an IDEXX Procyte DX hematology analyzer (iDEXX, Westbrook, ME). Blood smears were prepared, stained with modified Wright's stain, examined in a blinded fashion by a board-certified veterinary clinical pathologist (T.S.), and imaged using a Nikon Eclipse TE2000-U fluorescent microscope equipped with a photometrics CoolSNAP HQ$^2$ camera (Nikon Corporation, Tokyo, Japan). The blood was also centrifuged (1,500×G) for 15 min to obtain the serum for biochemical analysis using a Beckman Coulter AU680 analyzer (Beckman Coulter, Brea, CA).

Statistical analysis—Statistical analyses were performed using Graph Pad Prism 7.0 software and R v4.0.5 (R Foundation for Statistical Computing, Vienna, Austria) software. All data are presented as mean±standard deviation and significances were assigned at *p<0.05, p<0.01, and *p<0.001. Significant differences between groups were determined using a 2-tailed Student's t-test. For survival evaluation, the Mantel-Cox Log-Rank test were performed to compare the survival curves of animals treated with i.v. DM11-Bdd or aldox-Bdd to other treatments. β-values were adjusted for multiple comparisons using the; Benjamini &. Hochberg method. All p-values are two-sided with statistical significance evaluated at the 0.05 alpha level, Ninety-five percent (exact) confidence intervals for all parameters were calculated to assess the precision of the obtained estimates.

Example 1: Bdd can be Exclusively Eliminated Via Renal Clearance

Figure 1C:
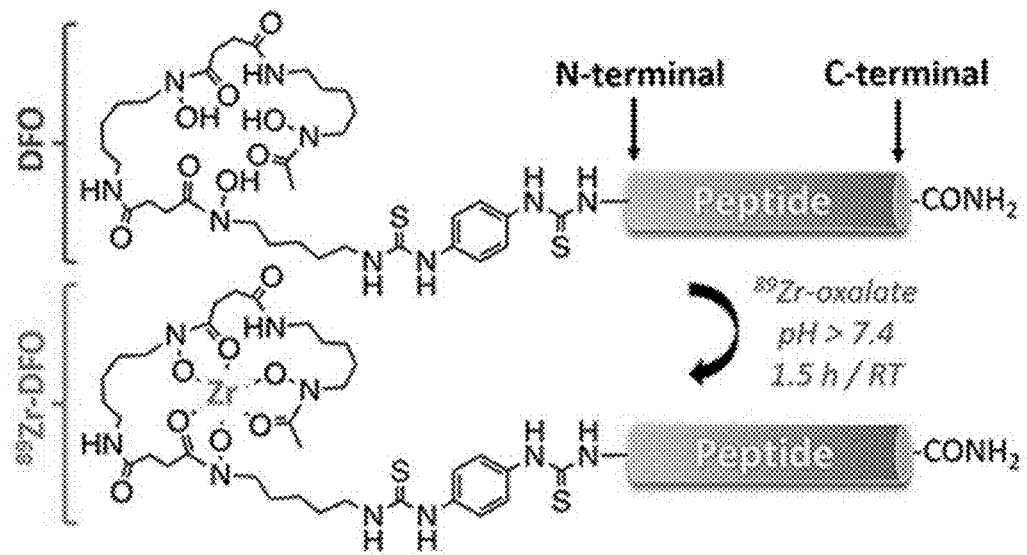

Bdd was designed in D-configuration to avoid degradation by protease enzymes in the blood circulation. It is composed of multiple D-aspartic acid (d) and β-alanine (B) residues (FIG. 1b). The aspartic acids contributed to the overall negative charge, preventing non-specific uptake by major organs and promoting renal clearance of the peptide. The B residues served as linkers to avoid the formation of a secondary structure. To investigate how the charges impacted Bdd's in vivo behavior, a panel of Bdd analogues were synthesized that were in L-configuration (BDD), neutral (BKD), carrying positive charges (BKK), and in pegylated form (PEG$_3$DD) for comparative studies. The peptides were labeled with 89-zirconium ($^{89}$Zr), a long-lived radioisotope (ti/2=78 h), which allowed the study of the pharmacokinetics (PK) and long-term biodistribution (BD) using micro positron emission and computerized tomography (PET/CT) imaging. The radiolabeled peptides ($^{89}$Zr-peptides) were synthesized by firstly conjugating a deferoxamine (DFO) chelator to the peptide in solid phase after amino acid elongation. $^{89}$Zr was then complexed with the resulting DFO-peptide conjugates in solution under a basic conditions (FIG. 1c).

Figure 1D:
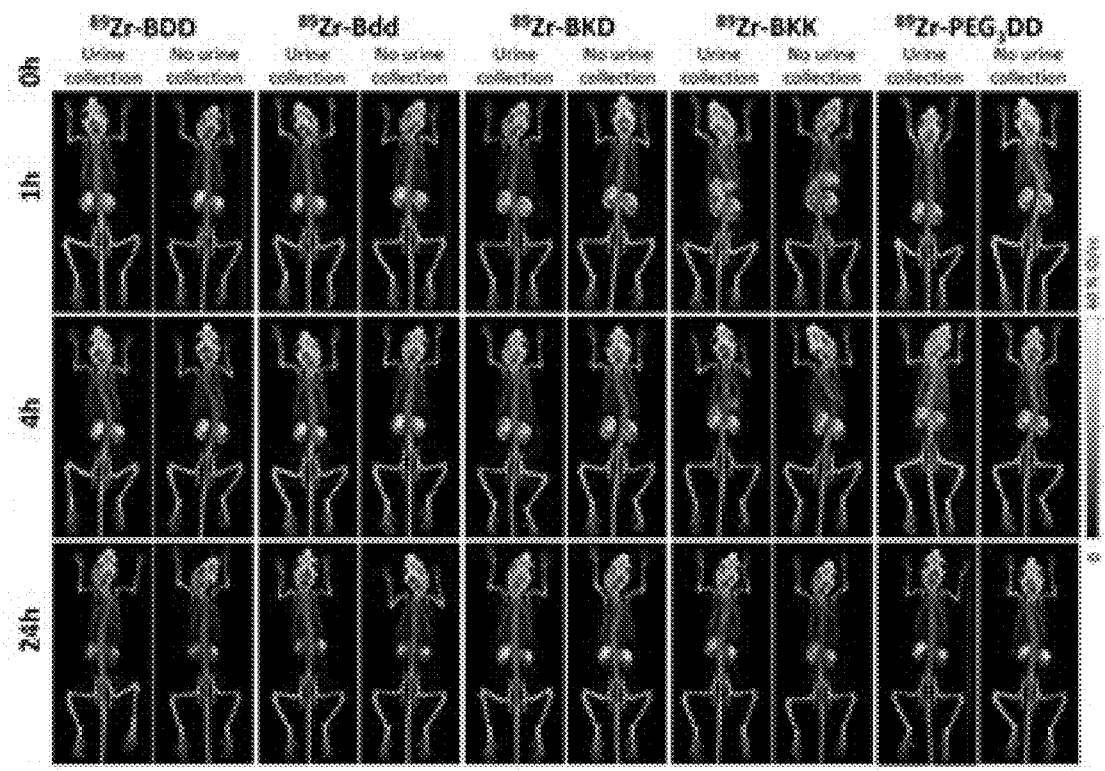
Figure 1E:
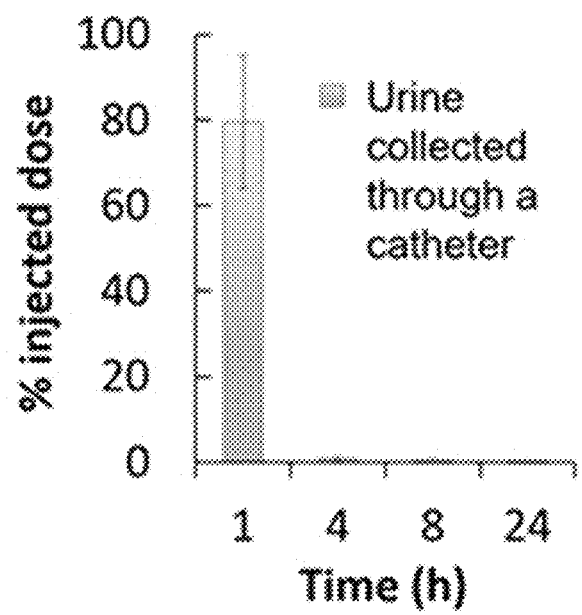
Figure 1F:
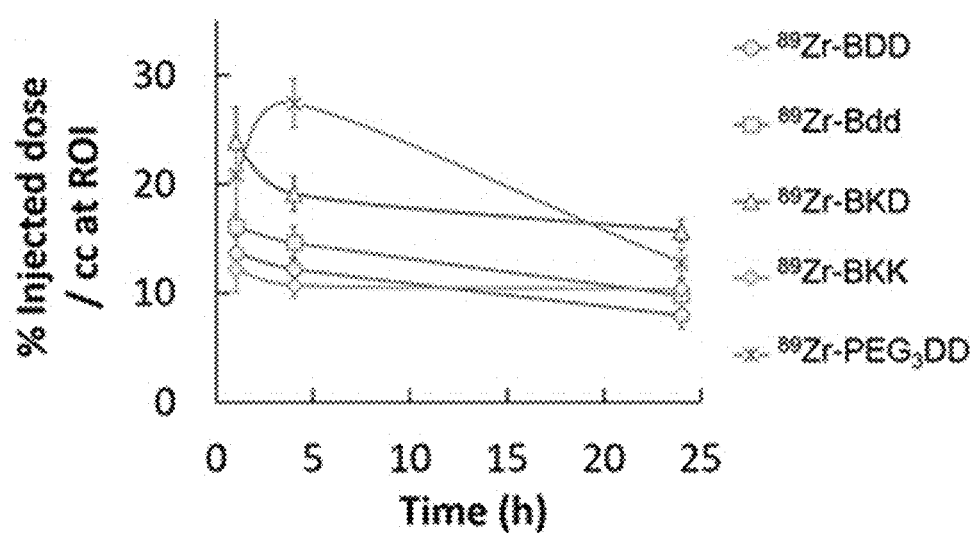
Figure 1G:
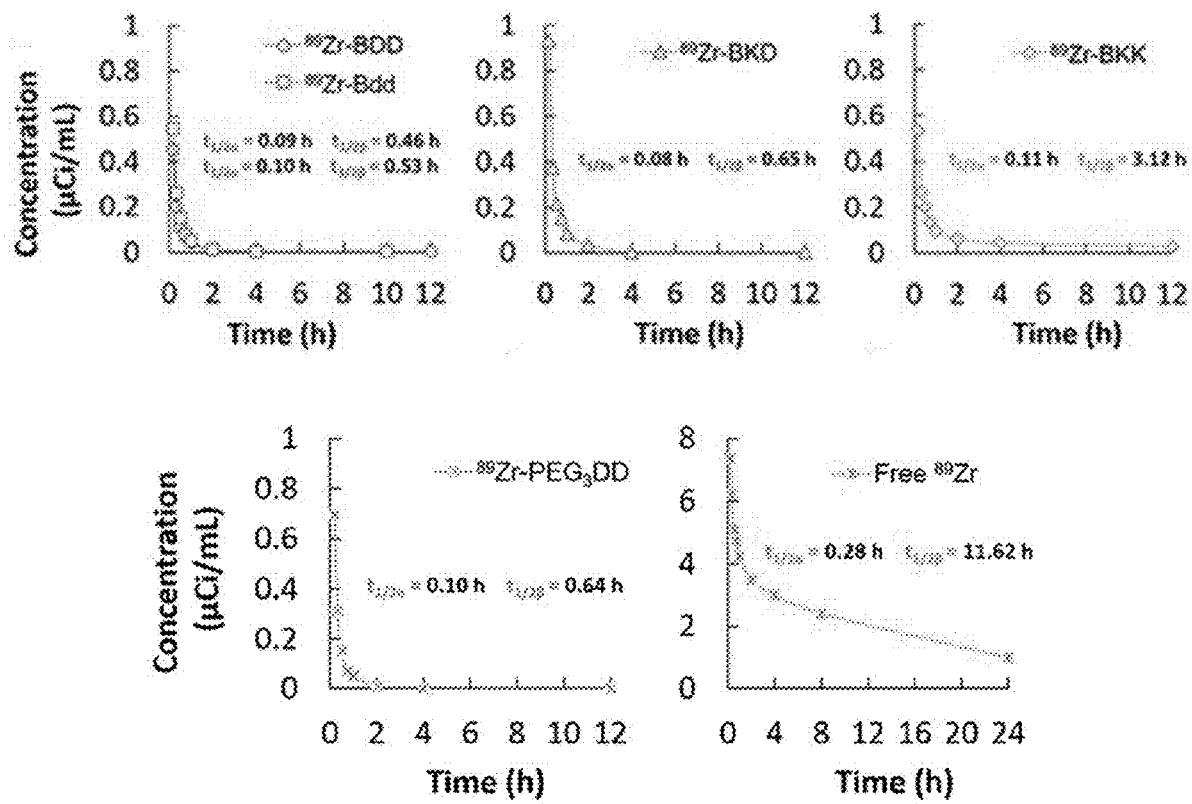
Figure 1H:
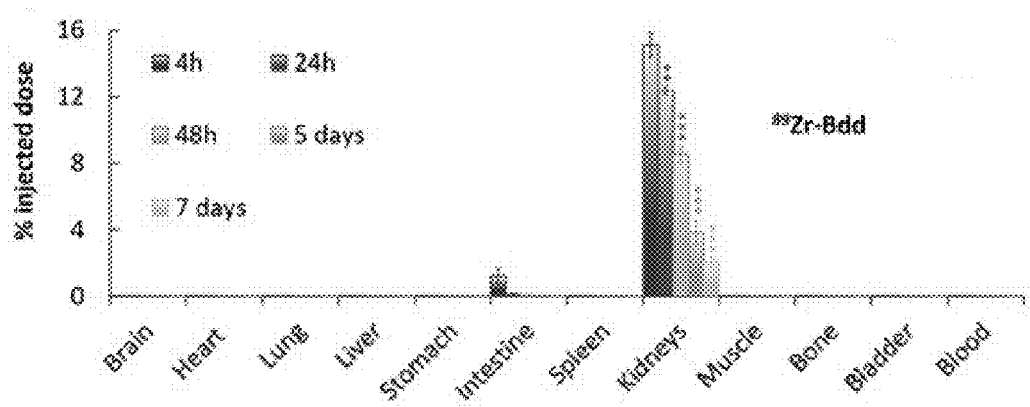
Figures 7A, 7B:
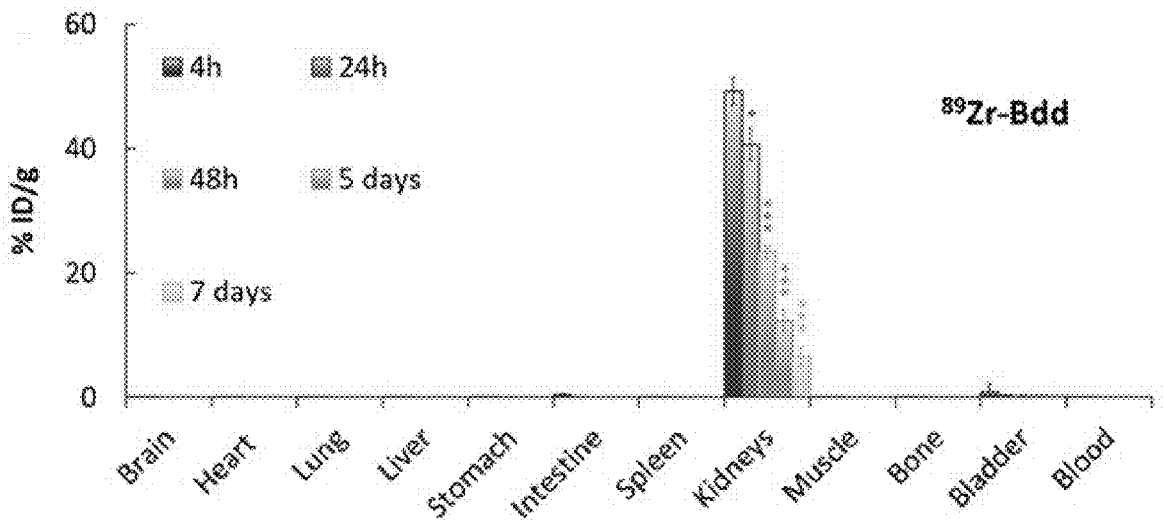
FIGS. 7A-B.

The results showed that $^{89}$Zr-Bdd and $^{89}$Zr-BDD displayed minimal off-target delivery (FIG. 1d). Radioactivity was not detected in the major organs, except the kidneys. Both peptides were rapidly excreted into the urine within 1 h after i.v. administration, as confirmed by the absence of radioactivity in the bladders that were catheterized and emptied prior to imaging. The results also showed that as high as 80% of the total injected dose (ID) was in the first urine sample collected from the animals injected with $^{89}$Zr-Bdd (FIG. 1e), suggesting that the peptide was filtered via the glomerulus with minimal reabsorption. On the other hand, the positively charged $^{89}$Zr—BKK was delivered to the liver in addition to the URS (FIG. 1d). Renal uptake among the peptide analogues was also compared. Except for an initial increase in PEG$_3$DD, they all showed reduced accumulation in kidneys over time (FIG. 1f). To determine the PK profile, experimental data was fit into a two-compartment model. The results showed that all the peptide analogues displayed shorter half-lives compared to the free $^{89}$Zr (FIG. 1g). $^{89}$Zr-Bdd had a terminal half-life of 0.53 h and rapid plasma clearance (FIG. 7a). An end-point biodistribution study of $^{89}$Zr-Bdd was then performed. The results were in good agreement with the imaging and PK studies. No peptide in major organs or blood circulation was detected 4 h after i.v. injection (FIG. 1h & FIG. 7b). Despite of the rapid clearance, a 15.1% of $^{89}$Zr-Bdd's ID was found in kidneys, which decreased to 2.1% after 7 days.

Example 2: As a Carrier of Hydrophobic Molecule

Figure 2A:
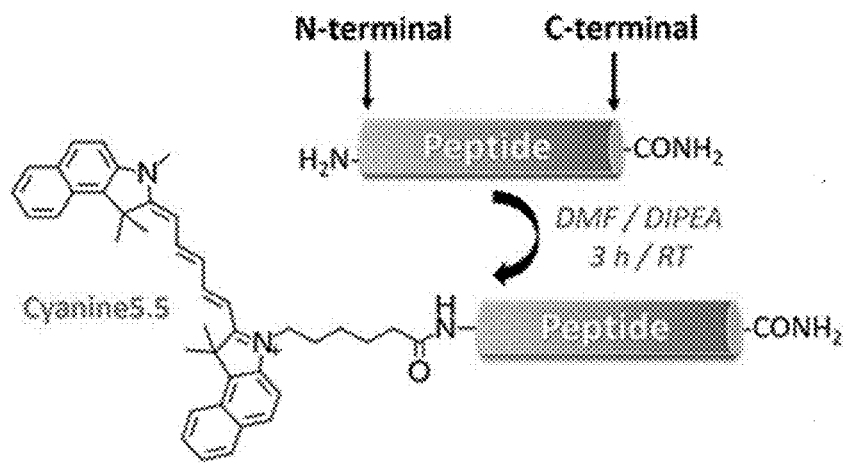
FIGS. 2A-E. Bdd effectively distributes the conjugated Cyanine5.5 fluorophore to the urinary system.
Figure 2B:
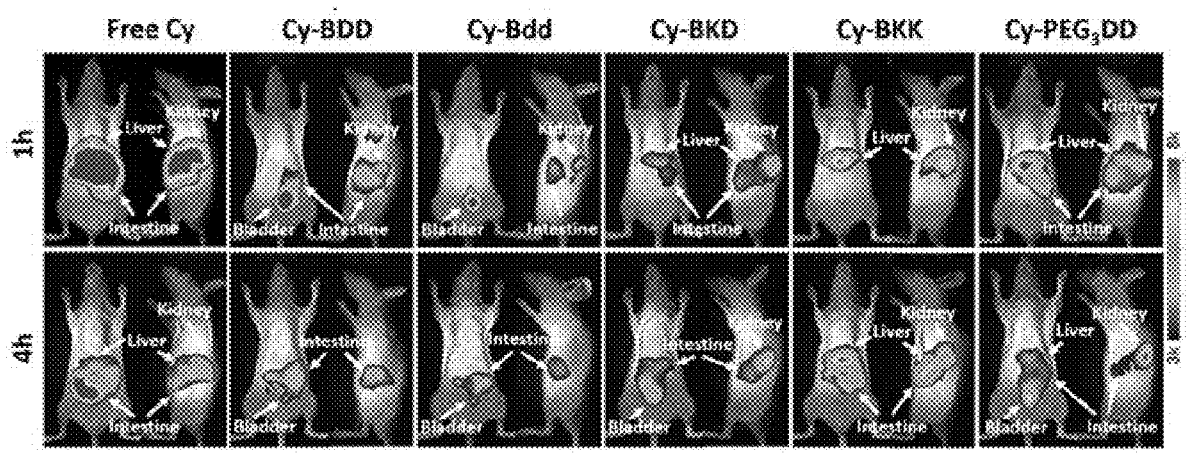
Figure 2C:
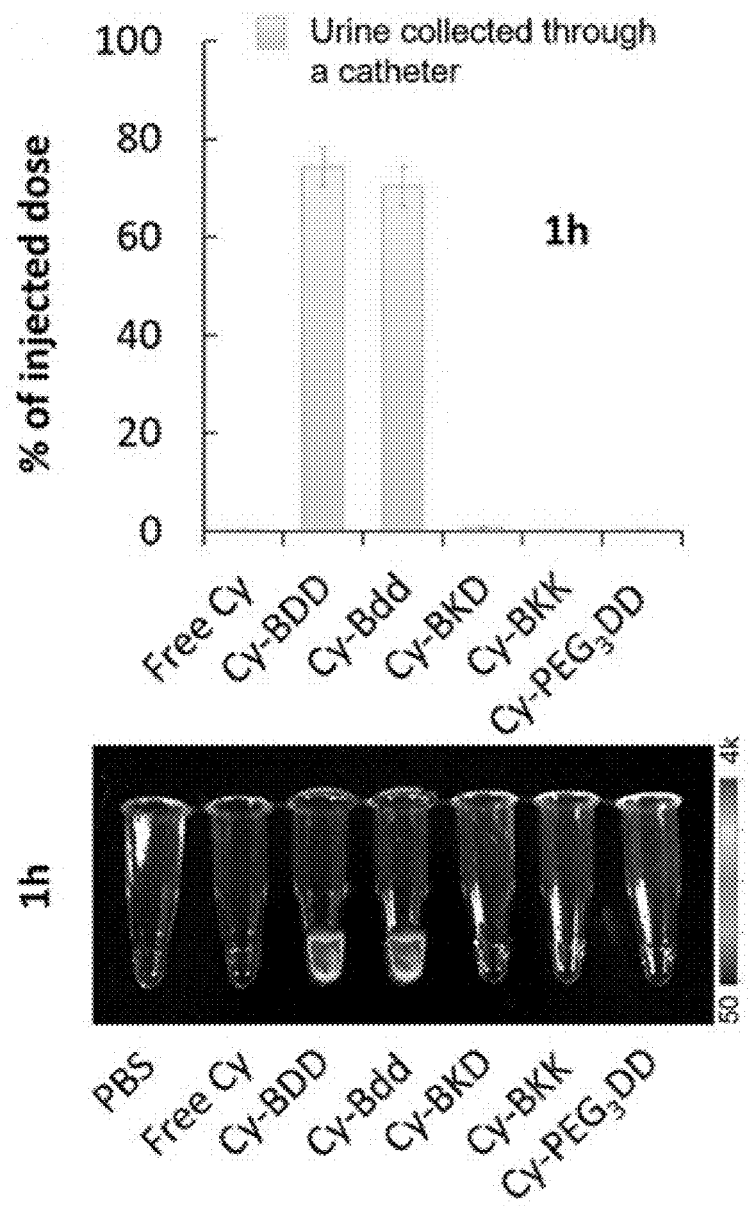
Figure 2D:
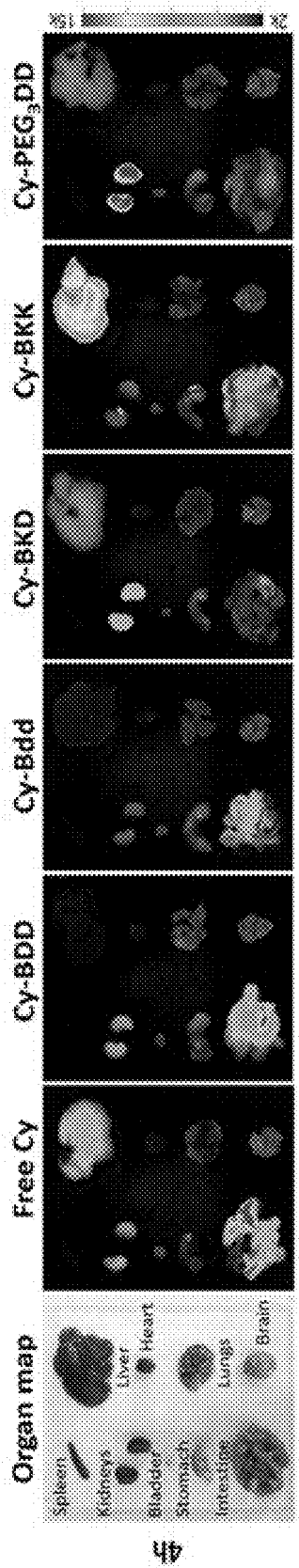
Figure 2E:
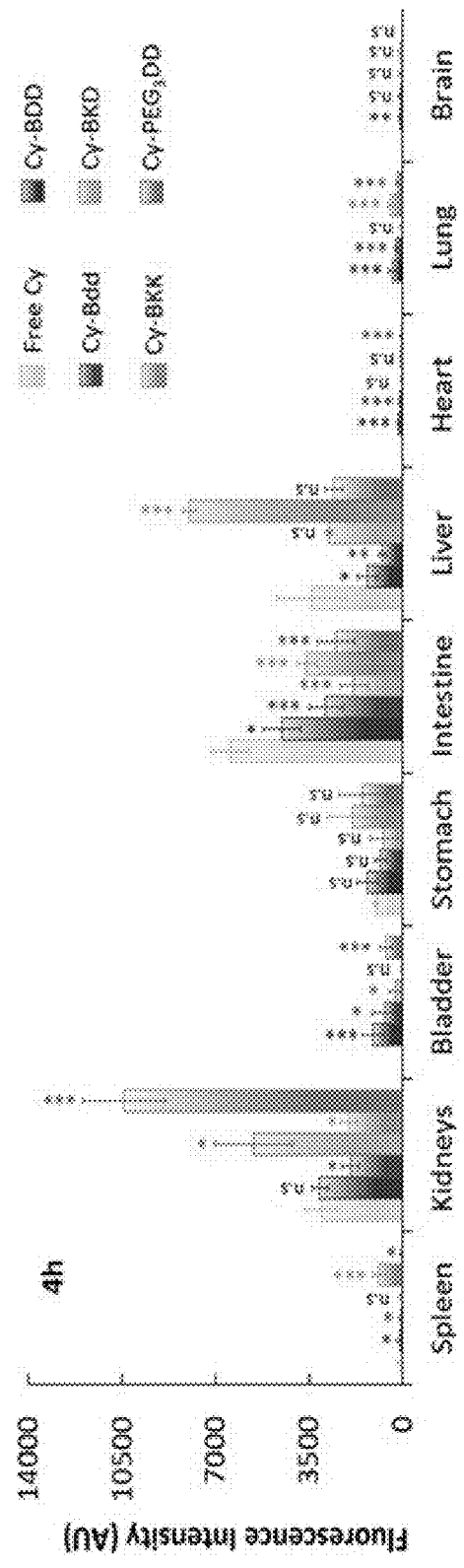

Most chemotherapeutics are hydrophobic molecules that display unfavorable PK and BD, leading to off-target delivery and undesired toxicity. Bdd's rapid renal clearance could be beneficial for promoting drug delivery to the URS. To demonstrate that, hydrophobic Cyanine5.5 fluorophore (Cy) was covalently attached as a drug model to the peptide analogues (FIG. 2a) and compared the resulting conjugates (Cy-peptide) for in vivo delivery. Both Cy-Bdd and Cy-BDD could be rapidly eliminated via renal clearance. They reached the animals' bladders 1 h after i.v. injections (FIG. 2b), with as high as 70-75% ID presented in the urine (FIG. 2c). On the other hand, Cy-BKD, Cy-BKK, Cy-PEG3DD, and free Cy were mainly taken up by the liver. Ex vivo imaging of the harvested organs (FIG. 2d) was also performed. As expected, the accumulation of Cy-Bdd and Cy-BDD in kidneys was minimal compared to other conjugates (FIG. 2e). However, unlike $^{89}$Zr-Bdd, trace amounts of Cy-Bdd and Cy-BDD were taken up by the stomach, liver, and intestines. The biodistribution differences were likely attributed to the replacement of a negatively charged $^{89}$Zr-DFO by the hydrophobic Cy. Overall, Bdd could be used for delivering hydrophobic molecules, such as Cy, to the URS while maintaining the comprehensive UDD properties.

Example 3: As Carrier of Chemotherapeutics

Figure 3A:
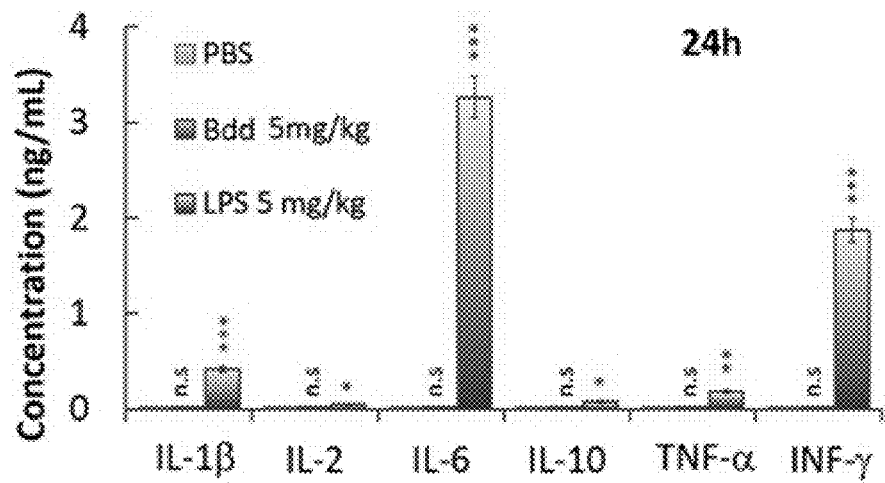
FIGS. 3A-I. Bdd as a carrier of chemotherapeutics.
Figure 3B:
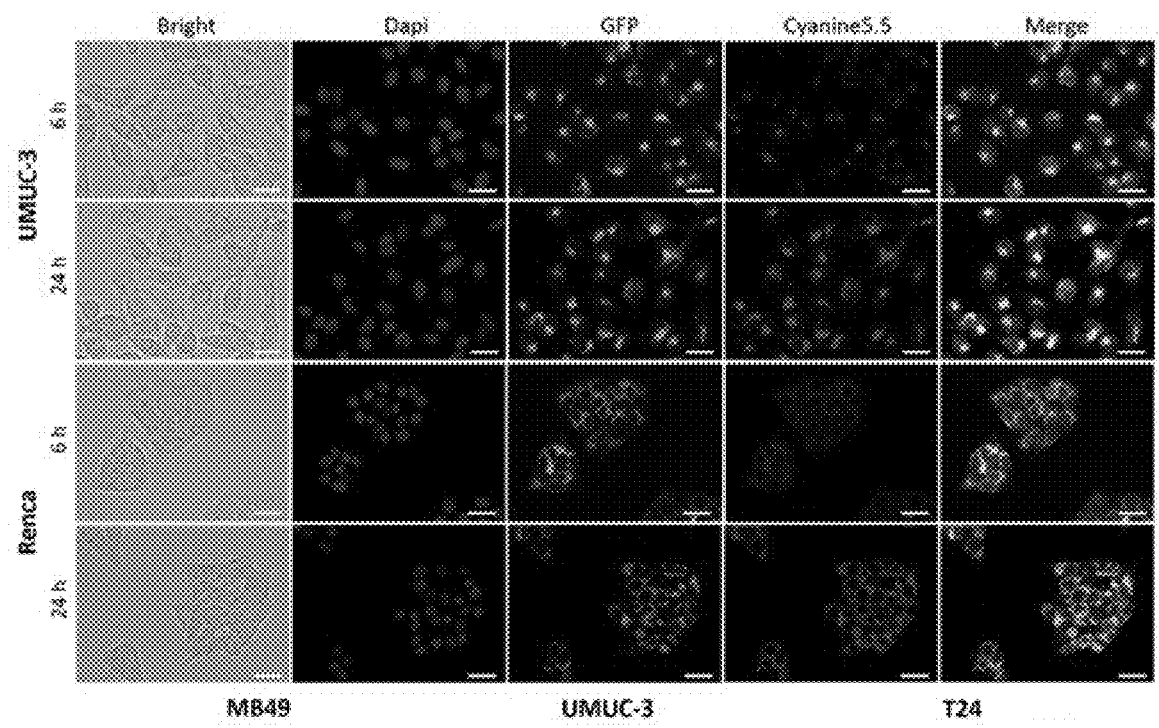
Figure 3C:
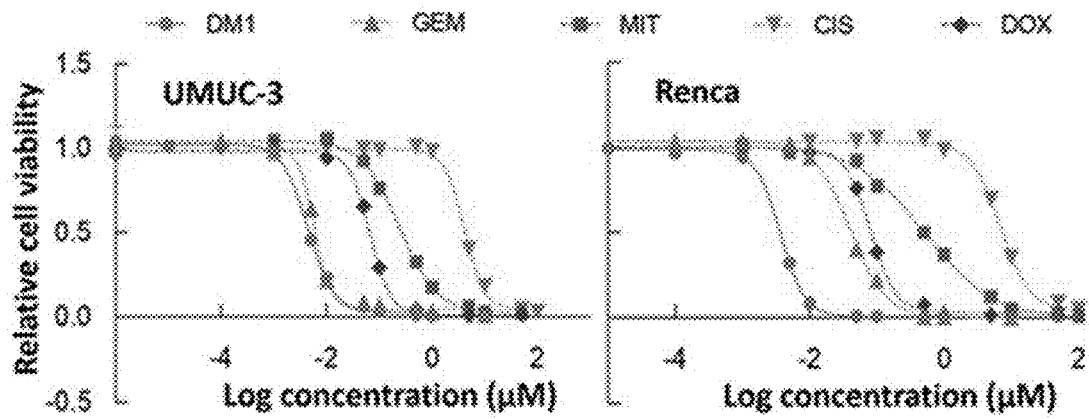
Figure 3D:
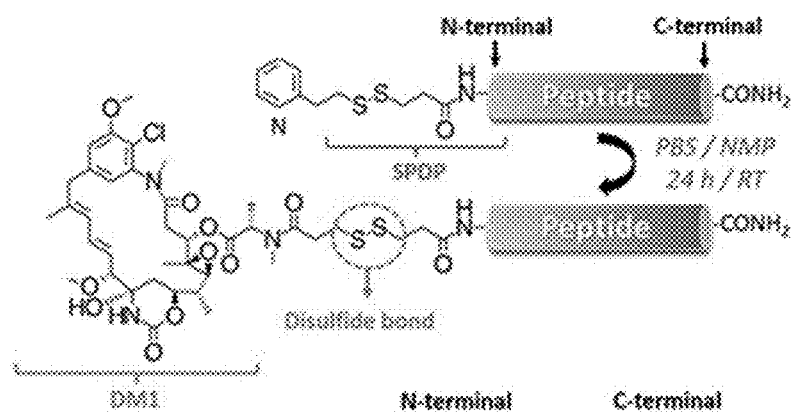
Figure 3E:
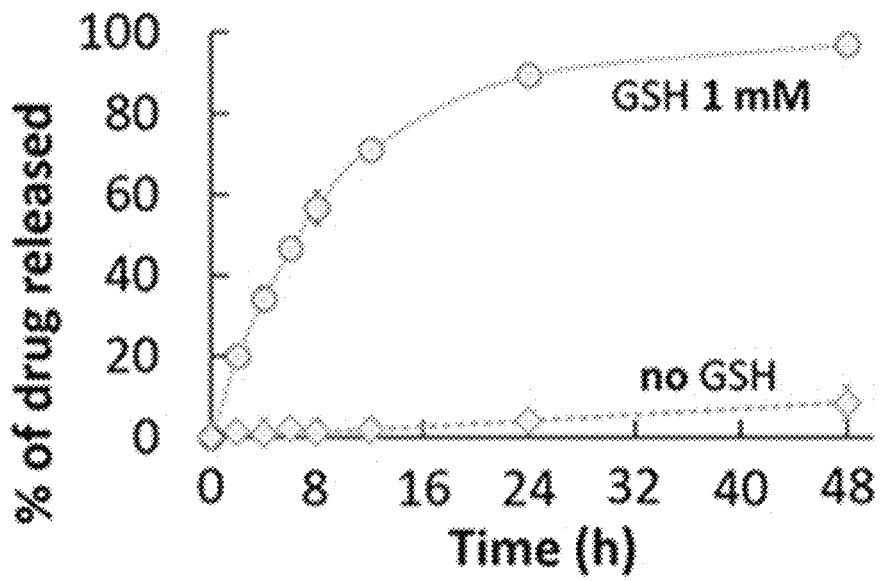
Figure 3F:
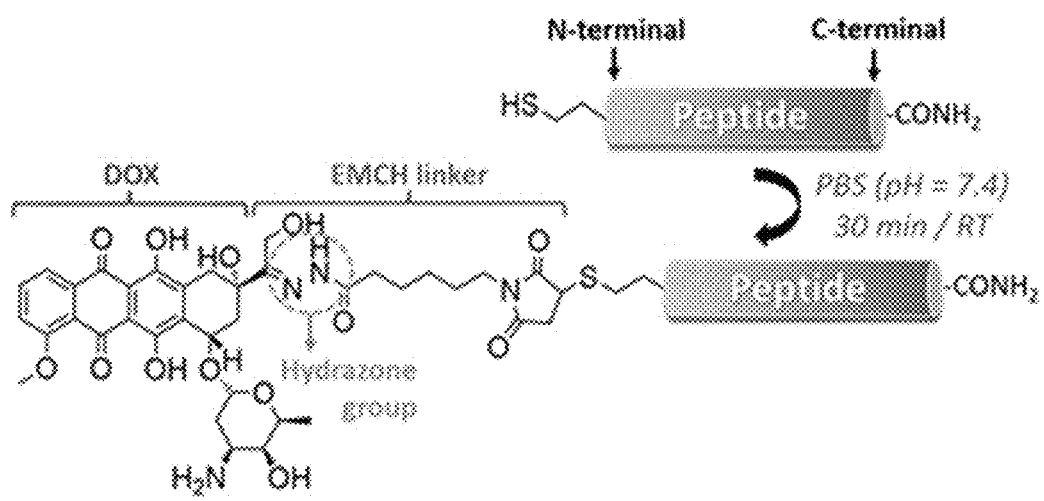
Figure 3G:
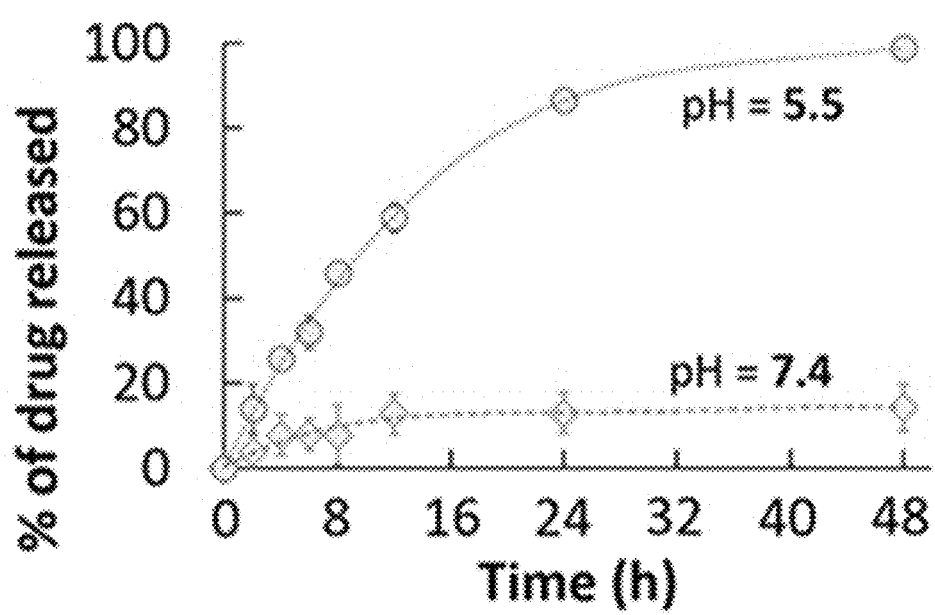
Figure 3H:
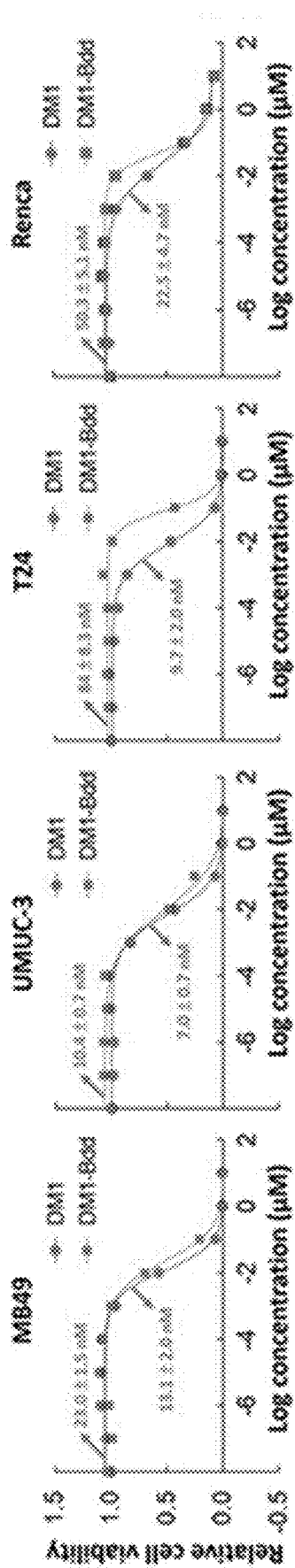
Figure 3I:
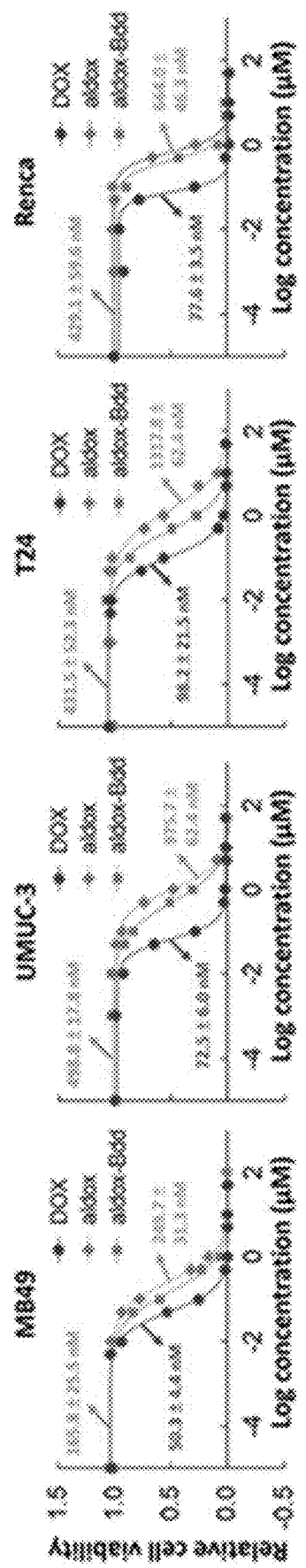

The Bdd's excellent UDD properties prompted further investigation of delivery of chemotherapeutics for NMIBC treatment. Many peptides are immunogenic. It was first confirmed that the Bdd peptide did not trigger innate immune responses. There was no increase of inflammatory cytokine levels (IL-1β, IL-2, IL-6, IL-10, TNF-α, and INF-γ) in the plasma of BALB/c mice 4 h after i.v. injection (FIG. 3a). Using the fluorescence C$_y$-Bdd, it was confirmed that the peptide could be taken up by human BC (UMUC-3) and murine kidney cancer (Renca) cells (FIG. 3b). Overlapping of the peptide (red) and lysosome (green) fluorescence was observed, suggesting that cellular uptake of the peptide mainly occurred via endocytosis. As proof-of-principle, emtansine (DM1) was selected, a potent microtubule inhibitor, as a drug candidate. Compared to other conventional chemotherapeutics, DM1 was more potent than cisplatin (CIS), doxorubicin (DOX) and mitomycin (MIT), and as effective as gemcitabine (GEM) against UMUC-3, with IC$_{50}$ values at the nanomolar (nM) range (FIG. 3c). The drug was also effective against Renca cell line. Next, a DM1-Bdd conjugate was synthesized by attaching DM1 to Bdd via a cleavable disulfide linker (FIG. 3d), enabling drug release in a reducing environment, such as in the presence of intracellular glutathione (GSH) (FIG. 3e). The chemistry for conjugating other chemotherapeutics was also established, such as aldoxorubicin (aldox), to Bdd (FIG. 3f). Aldox is a DOX derivative modified with a hydrazone linker, which is known to be sensitive to the acidic lysosome and tumor microenvironment. The drug release from aldox-Bdd conjugate was pH-dependent (FIG. 3g). In terms of cytotoxicity, both DM1-Bdd and aldox-Bdd exhibited a similar potency to the corresponding free drugs against different murine (MB49) and human (UMUC-3 and T24) BC cell lines (FIGS. 3h-i).

Example 4: A More Effective Alternative to Conventional ITC

Figure 4A:
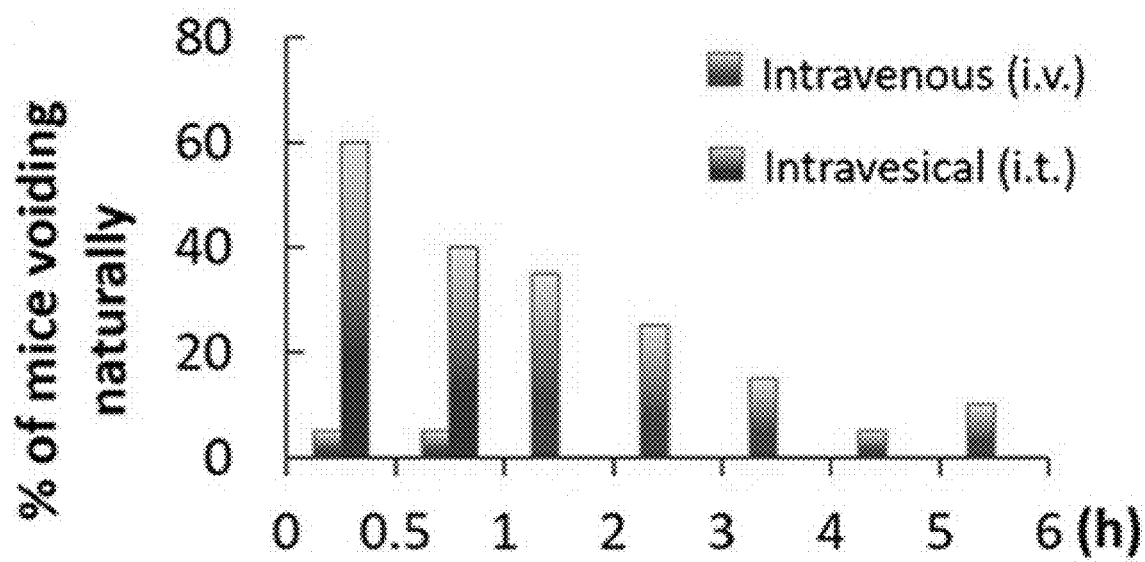
FIGS. 4A-J. Therapeutic efficacy of DM1-Bdd in treating bladder cancer.
Figure 4B:
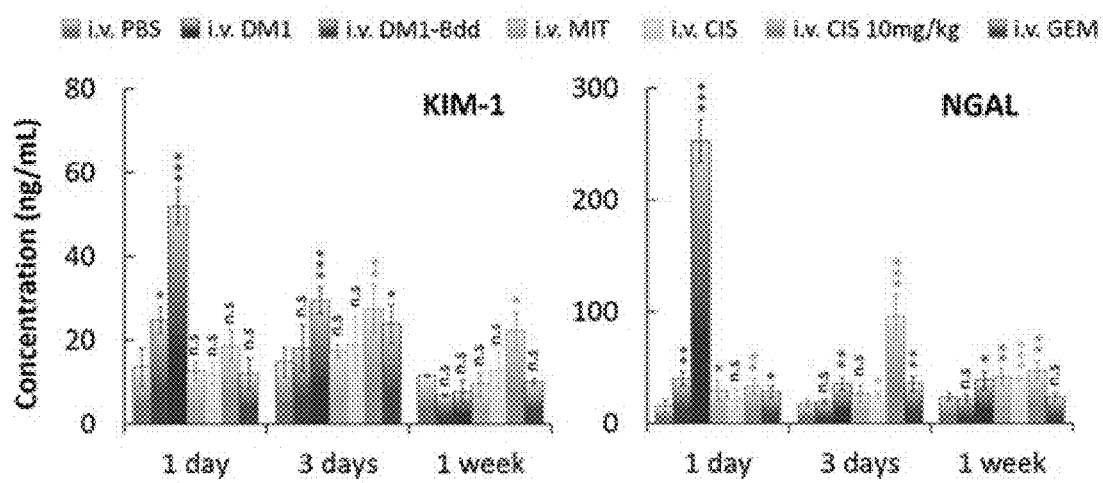
Figure 4C:
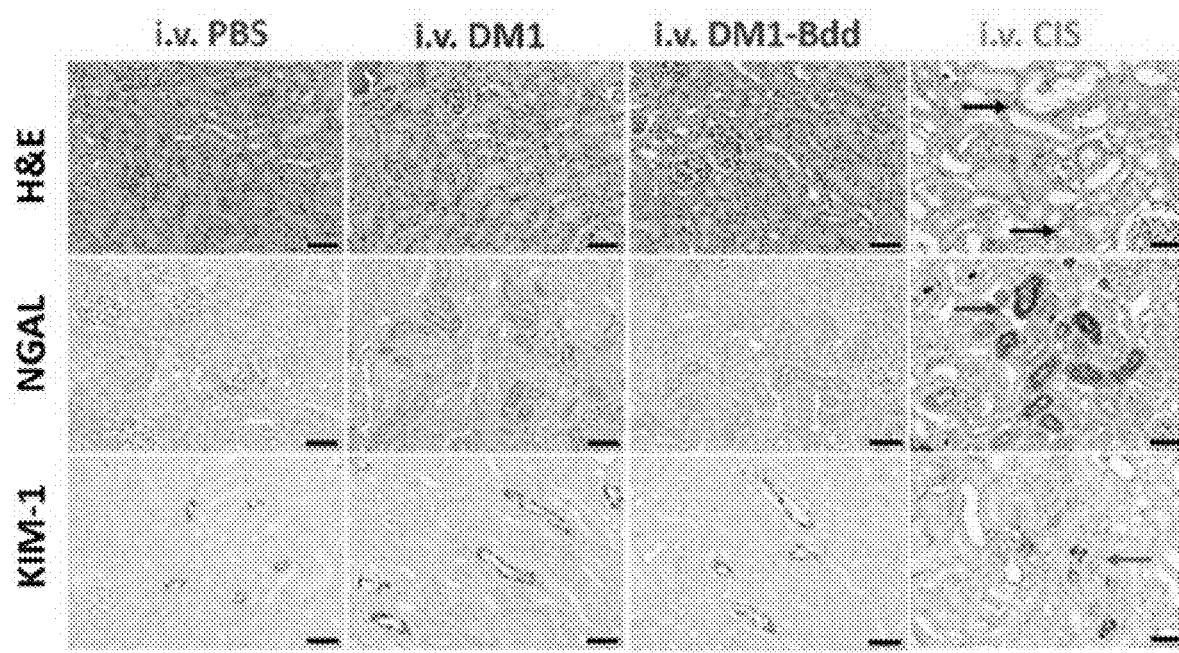

Unlike with intravesical (i.t.) administration, animals did not need to void shortly after i.v. injection (FIG. 4a). DM1-Bdd, administered through i.v. injection, should prolong the drug's bladder-dwelling time. This, together with the unique UDD properties, should offer a more effective (compared to ITC) and safer (compared to systemic chemotherapy) therapeutic option when using Bdd as a drug carrier. However, Bdd could temporarily accumulate in kidneys (FIGS. 1d and h). Therefore, prior to evaluating the therapeutic efficacy of DM1-Bdd, the tolerability of kidney to a single injectable dose in healthy mice was assessed. The results showed that DM1-Bdd slightly increased the levels of urinary tubular injury markers, kidney injury molecule-1 (KIM-1) and neutrophil gelatinase-associated lipocalin (NGAL), in the urine 1 day after the injection (FIG. 4b). The increases were minimal and transient, returning to basal levels within 3 days. Histologic examination at 3 days after drug administration did not reveal any abnormalities in the kidneys, with no elevation of the immunoreactivity of the tissue sections for KIM-1 and NGAL, when compared to PBS (FIG. 4c). In contrast, other i.v. chemotherapeutics, including DM1, MIT, CIS, and GEM, showed a continued induction of KIM-1 and/or NGAL at this time point. Dilation and degeneration of tubular epithelium in animals treated with a high dose of i.v. CIS (positive control) was also found (FIG. 4c).

Figure 4D:
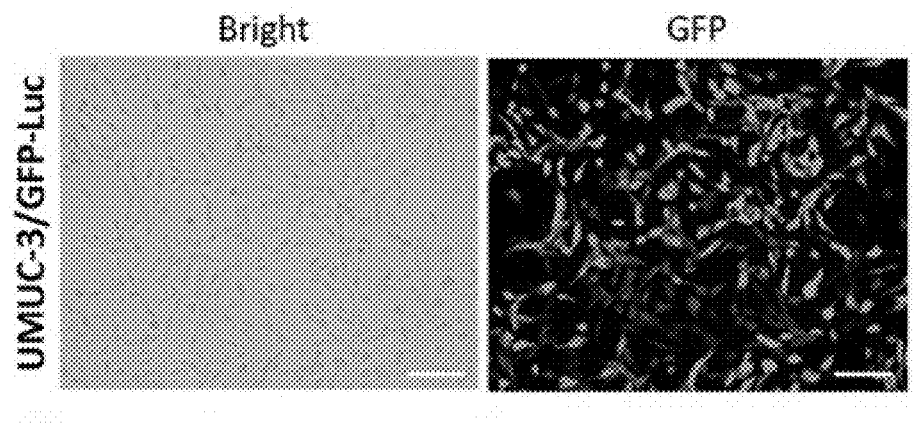
Figure 4E:
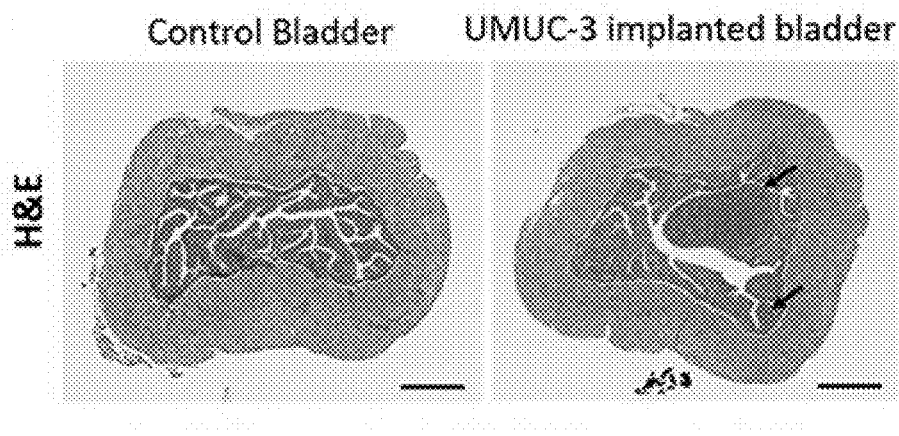
Figure 4F:
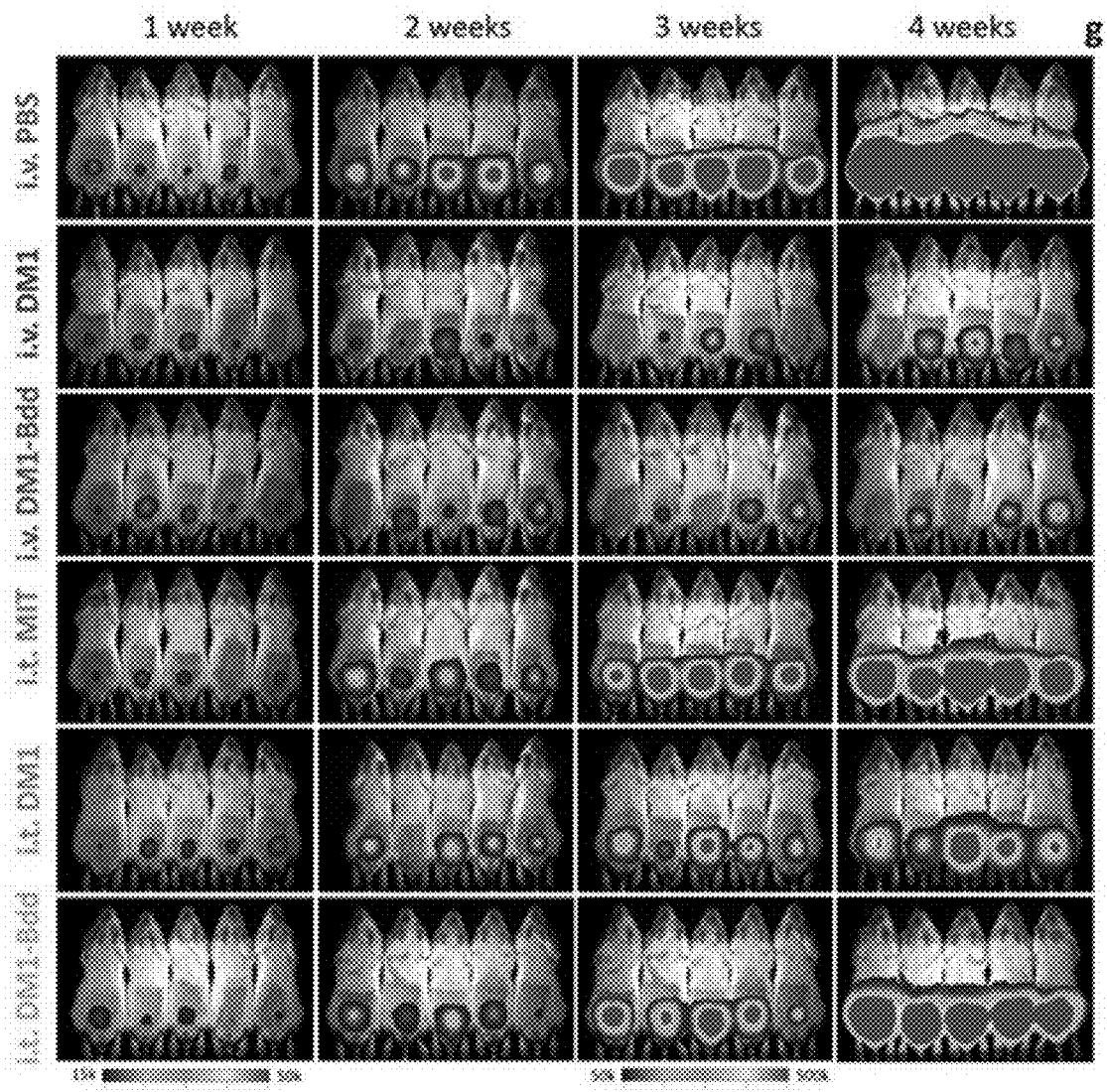
Figure 4G:
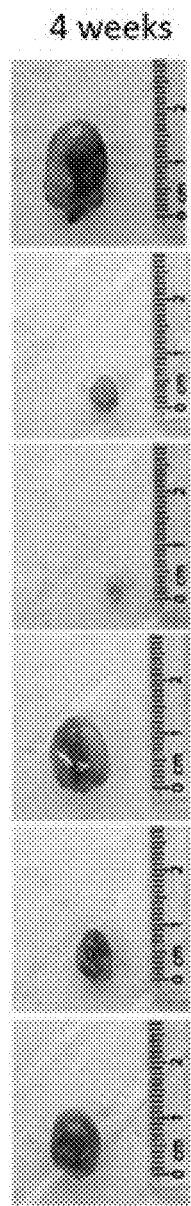
Figure 4H:
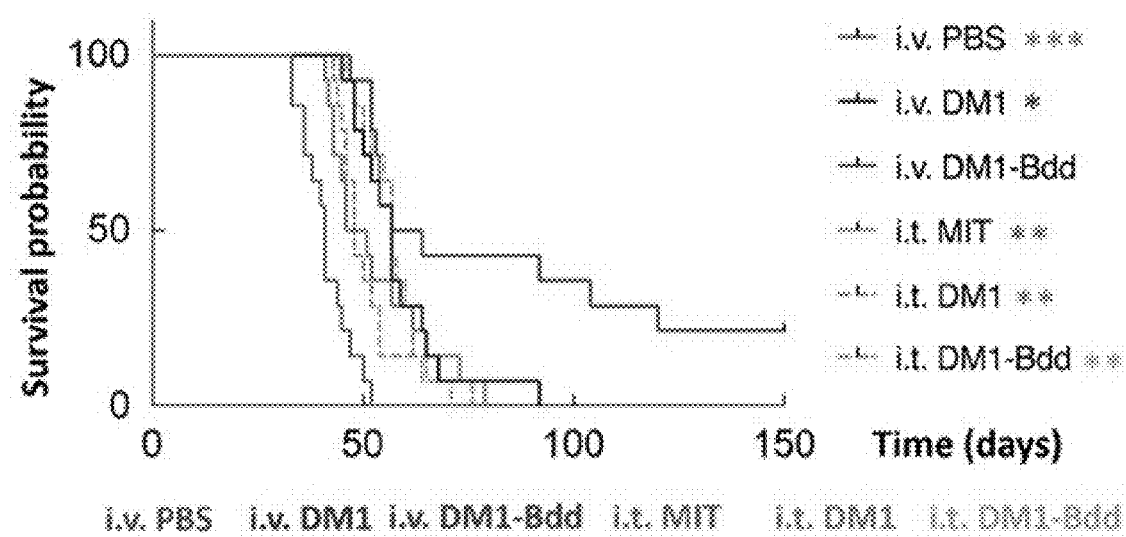
Figure 4I:
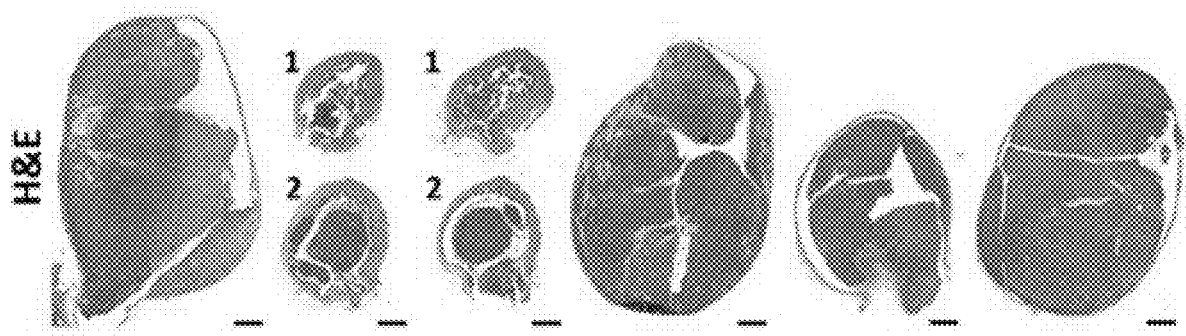
Figure 4J:
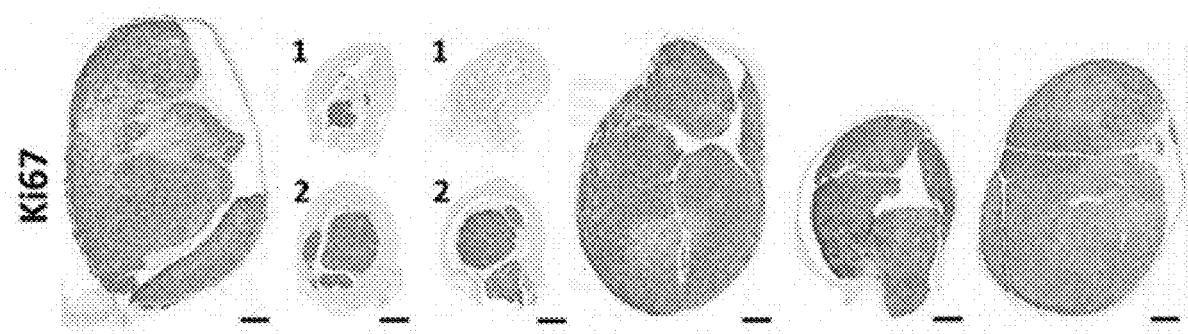
Figure 8A:
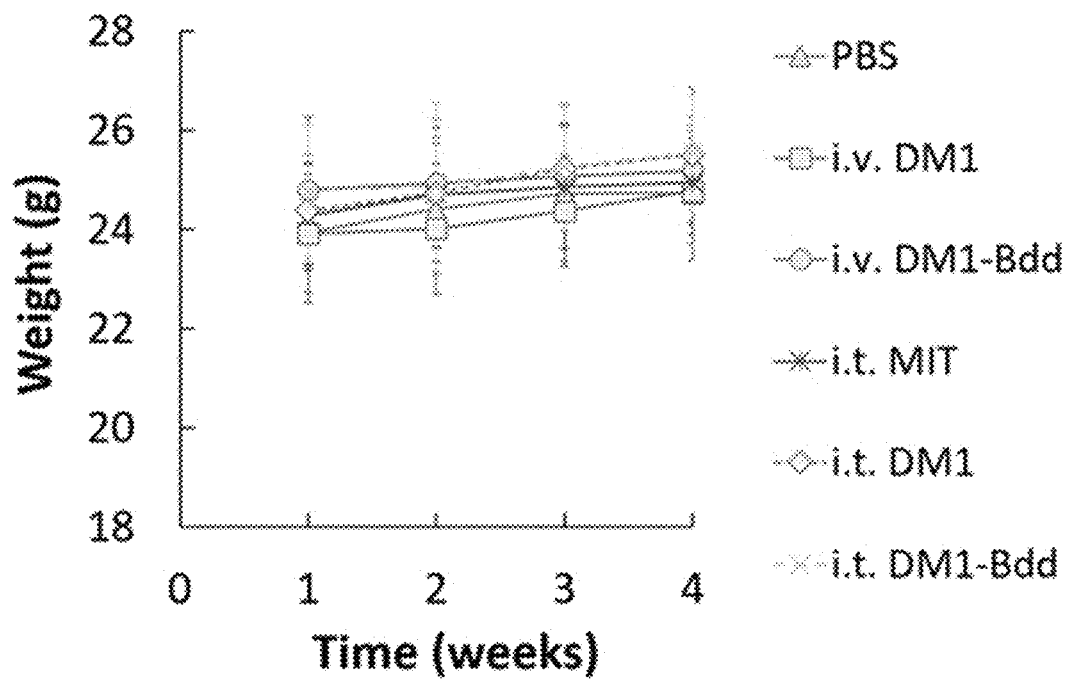
FIGS. 8A-G.
Figure 8B:
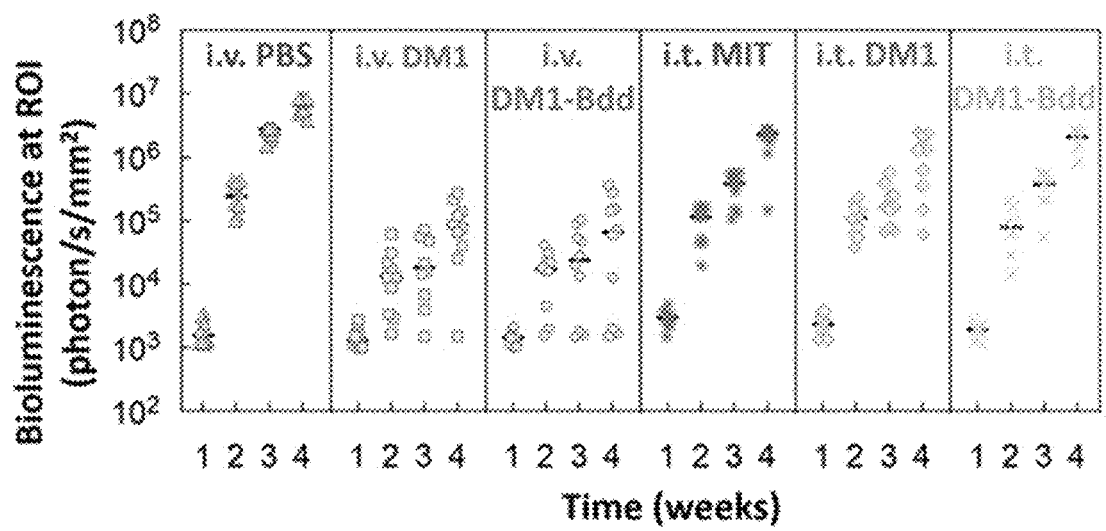
Figure 8C:
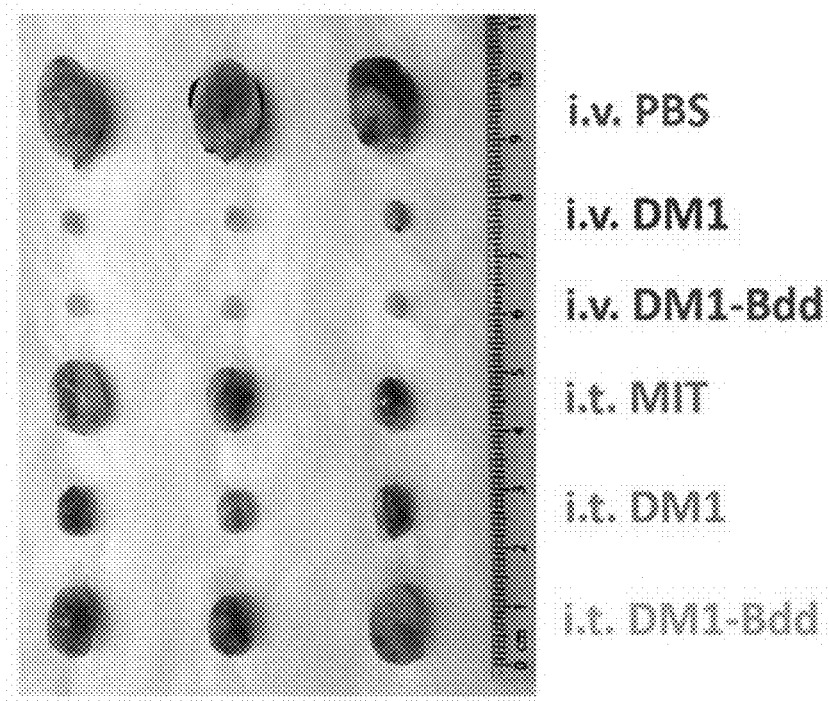
Figure 8D:
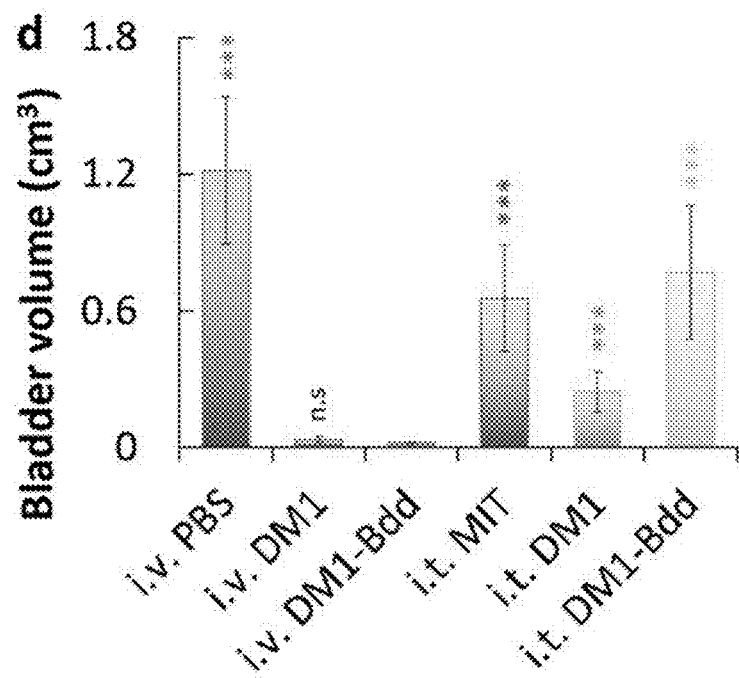
Figure 8E:
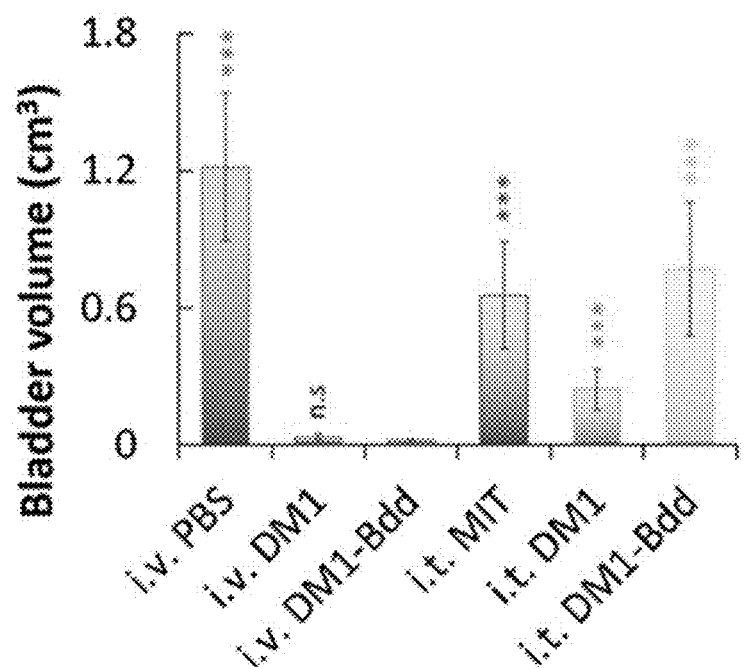
Figure 8F:
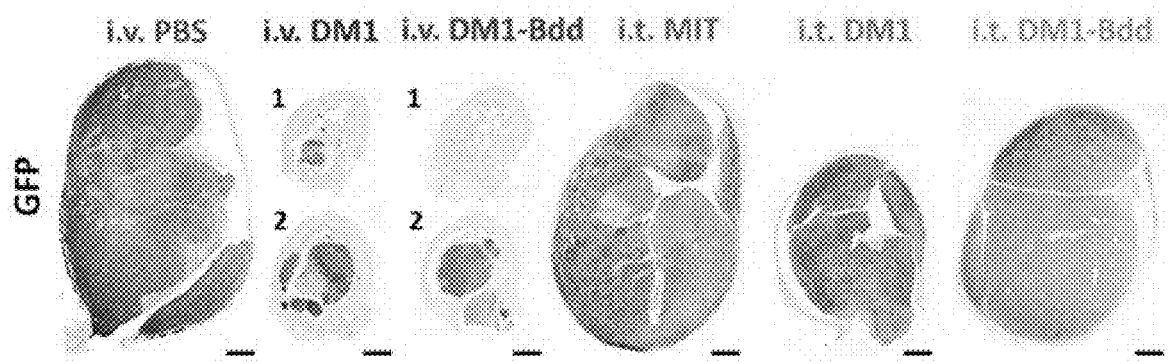
Figure 8G:
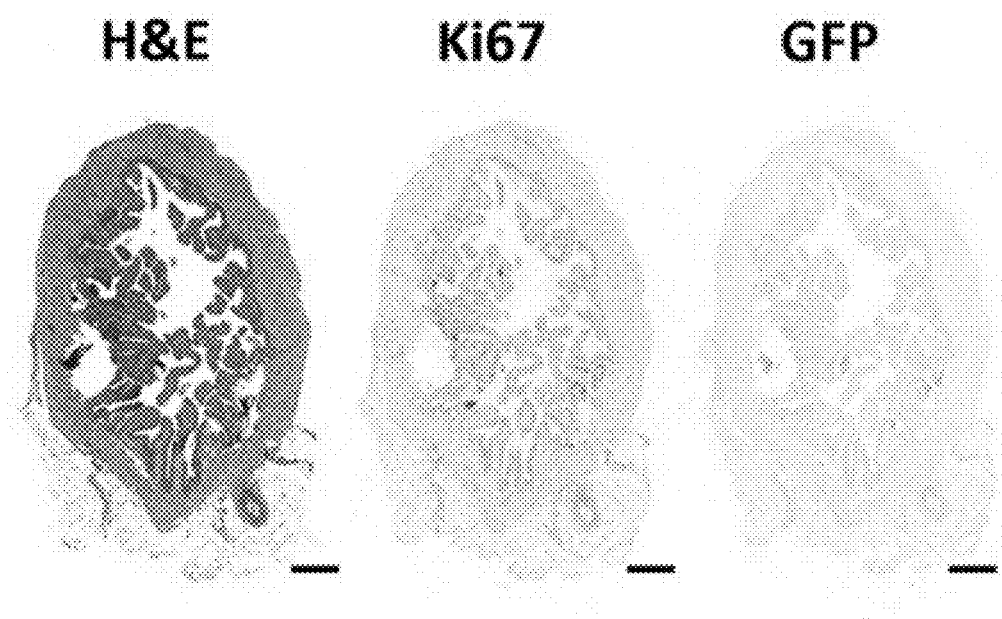
Figure 9A:
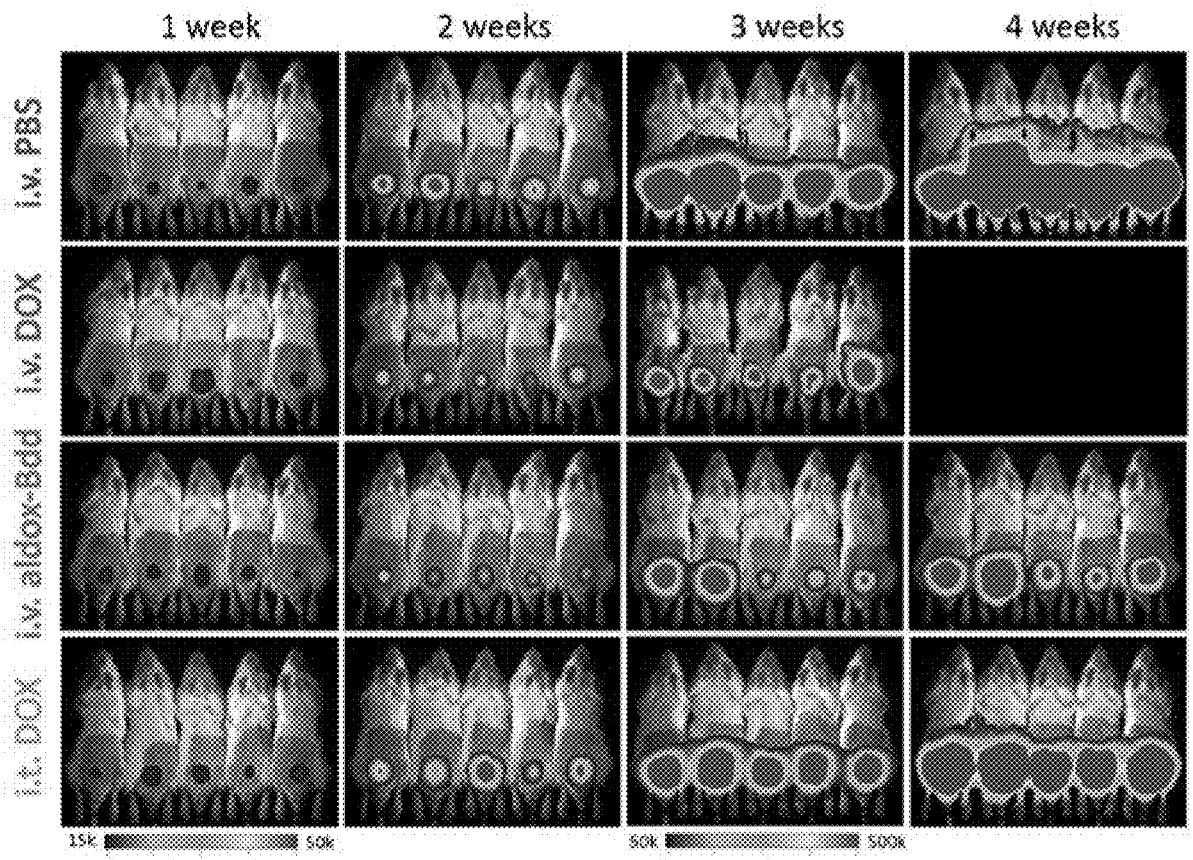
FIGS. 9A-E.
Figure 9B:
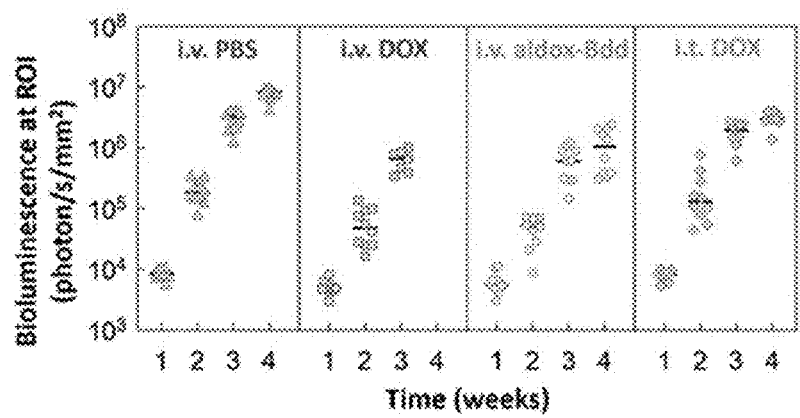
Figure 9C:
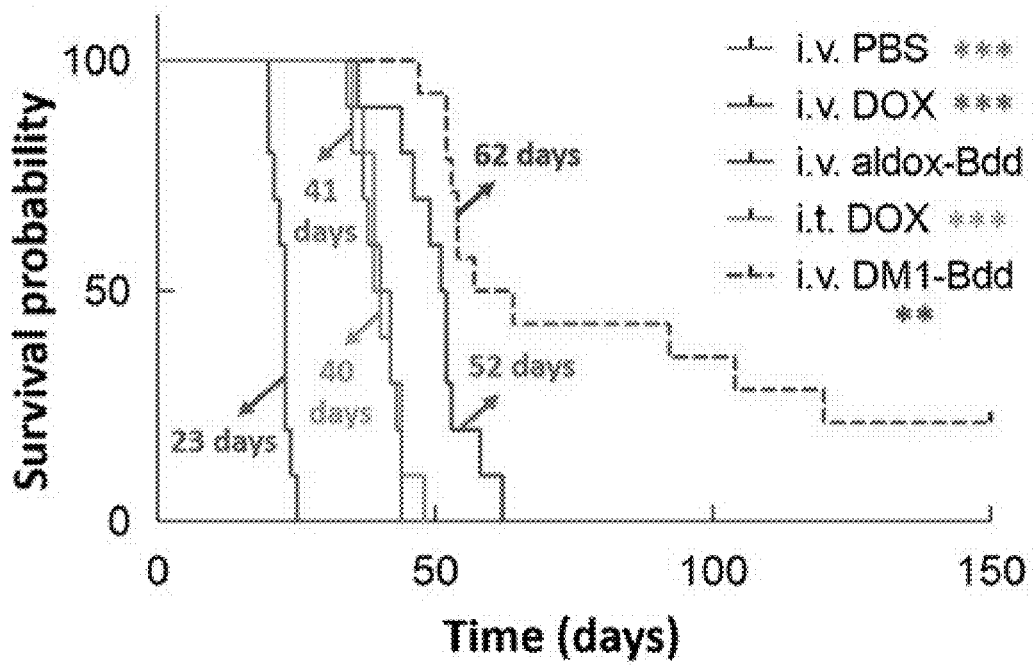
Figure 9D:
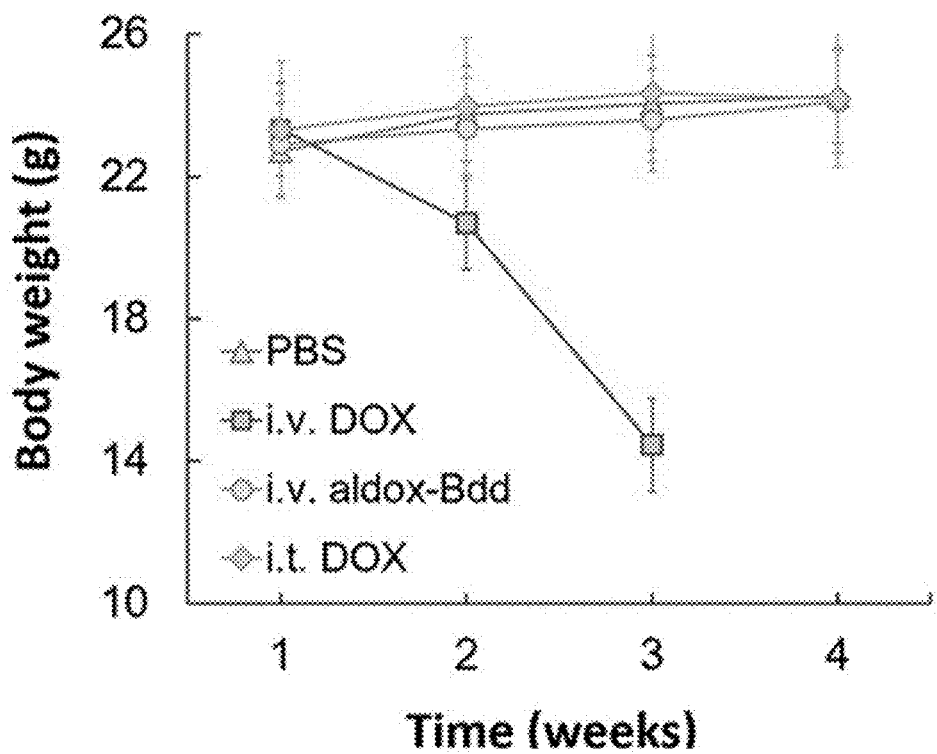
Figure 9E:
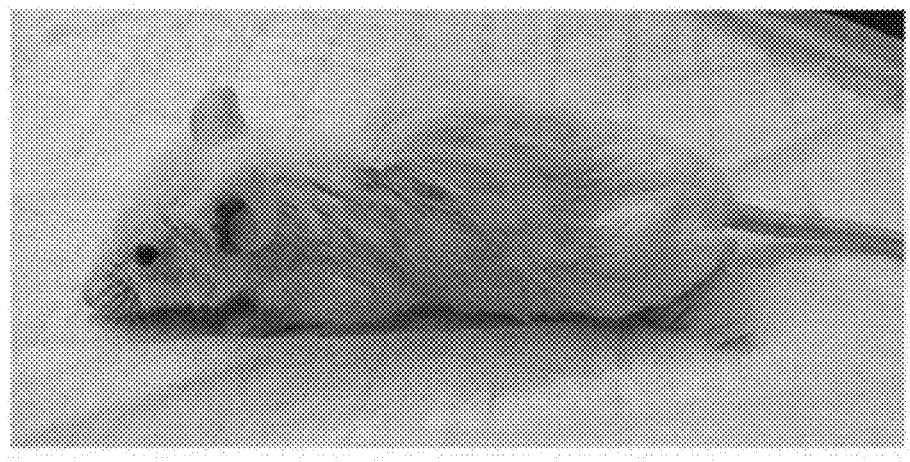

DM1-Bdd for treating mice bearing orthotopic human UMUC-3 tumors was then evaluated. Prior to implanting UMUC-3 cells into the animals' bladders, they were stably transduced with a dual luciferase and GFP reporter (FIG. 4d). This allowed monitoring of the disease progression with bioluminescence imaging. It was also confirmed that the established tumors, growing in the lamina propia, were non-invasive in nature and limited to the urinary bladder submucosa (FIG. 4e). Compared to the clinically used ITC (i.t. MIT), both i.v. DM1 and DM1-Bdd were more effective in inhibiting tumor growth (FIGS. 4f-g and FIGS. 8a-e) and prolonged animal survival (FIG. 4h). An i.v. injection of DM1-Bdd provided a better treatment outcome when compared to i.t. administration. According to the imaging data acquired during the 3 once-per-week treatments course, the anti-tumor activity of i.v. DM1-Bdd and DM1 was similar (FIG. 4f). However, those animals treated with i.v. DM1-Bdd showed a significant improvement in overall survival (36% versus 0% survived after 100 days). In a separate experiment, the therapeutic effect on tumor reduction was confirmed by histology. Tumors of the animals treated with i.v. DM1-Bdd were smaller (FIG. 4i). Immunohistochemistry revealed fewer GFP-positive cells and lower proportion of cells expressing the proliferation marker (Ki67), confirming the inhibition of tumor cell growth and proliferation (FIG. 4j and FIG. 8f). More importantly, DM1-Bdd treatment was curative for 21% of the animals. The survivor mice lacked gross and histologic evidence (using GFP and Ki67 immunostaining) of tumors, suggesting they were disease-free after 210 days (FIG. 8g). Bdd is a versatile delivery platform that can carry different chemotherapeutics. Aldox-Bdd was also able to prolong the animal survival compared to PBS and free DOX (FIGS. 9a-c). However, it was not as effective as DM1-Bdd in improving overall survival (FIG. 9c). Surprisingly, animals treated with free DOX had a shorter life expectancy compared to the PBS control, with all the animals continuously losing weight during DOX treatment (FIGS. 9d and e). They eventually died prior to receiving the final dose, suggesting drug-induced toxicity and mortality.

Example 5: Anatomic Flexibility

Figure 5A:
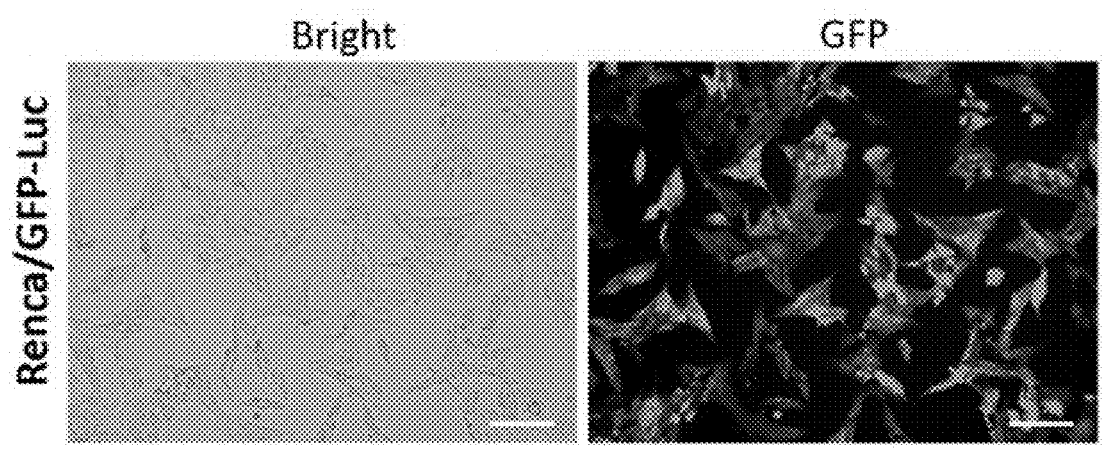
FIGS. 5A-H Therapeutic efficacy of DM1-Bdd in treating renal carcinoma.
Figure 5B:
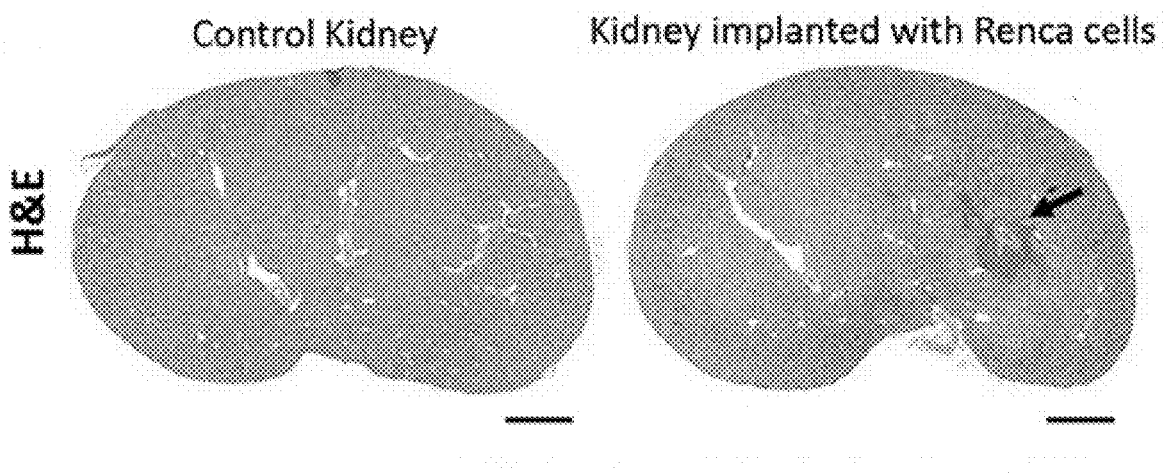
Figure 5C:
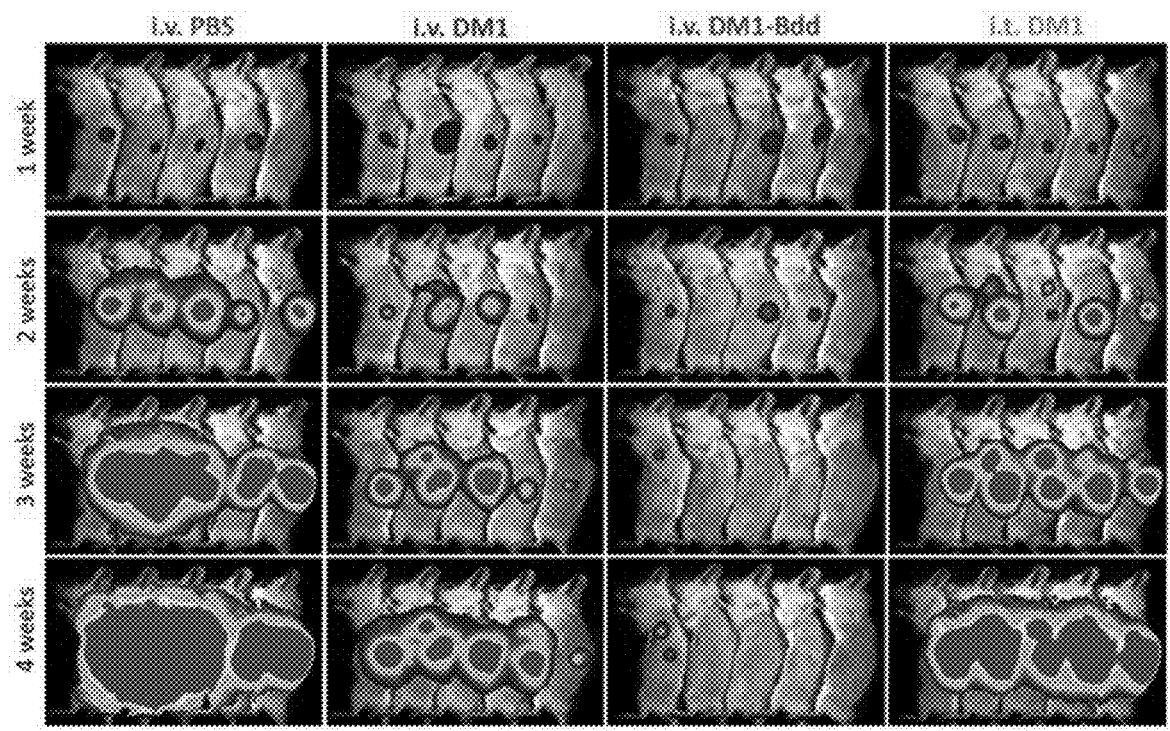
Figure 5D:
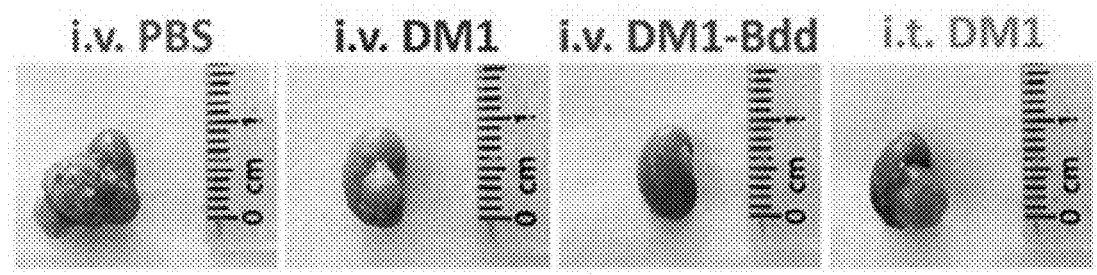
Figure 5E:
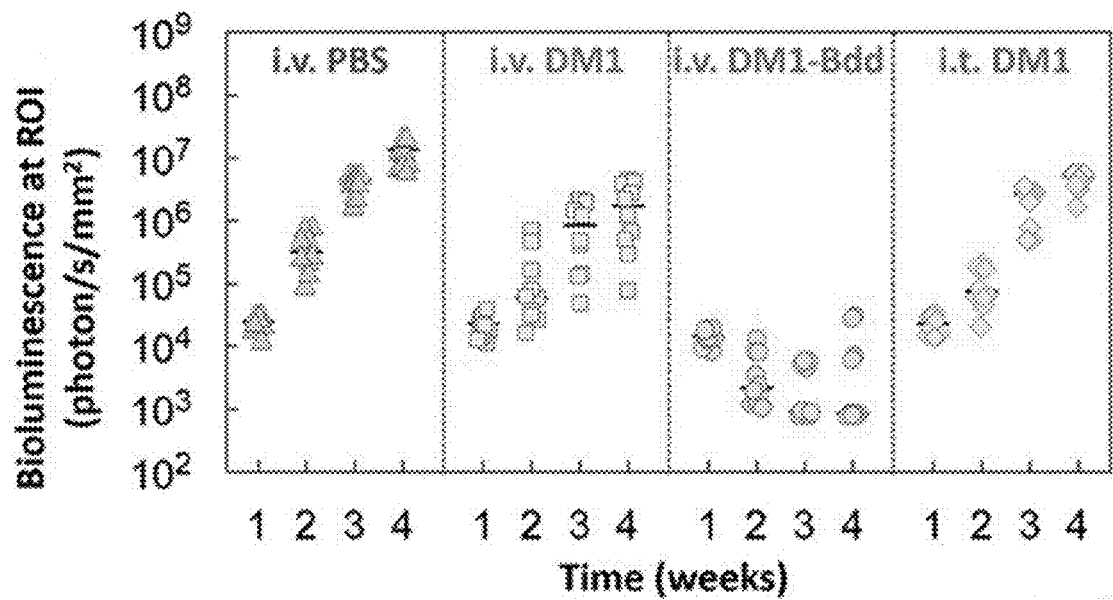
Figure 5F:
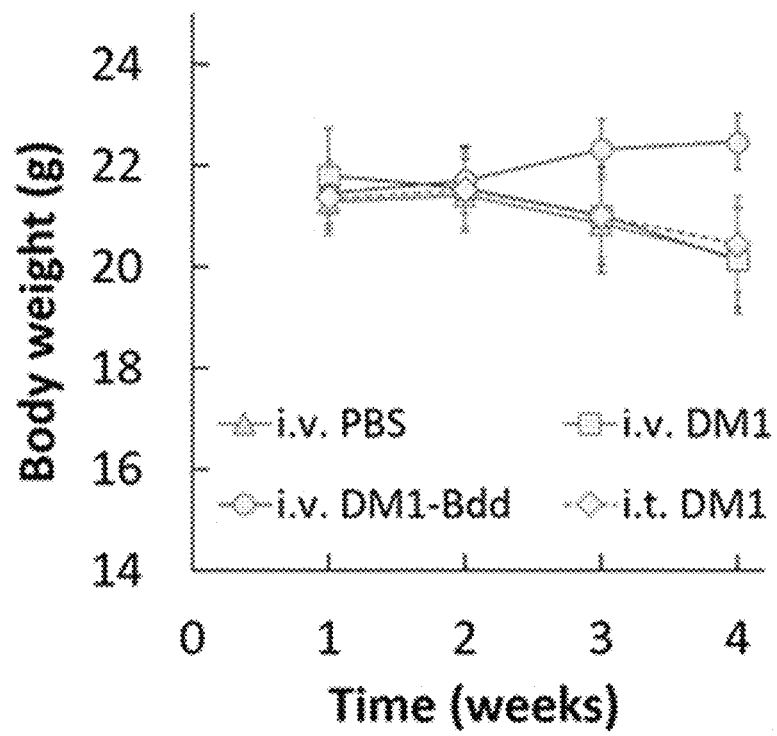
Figure 5G:
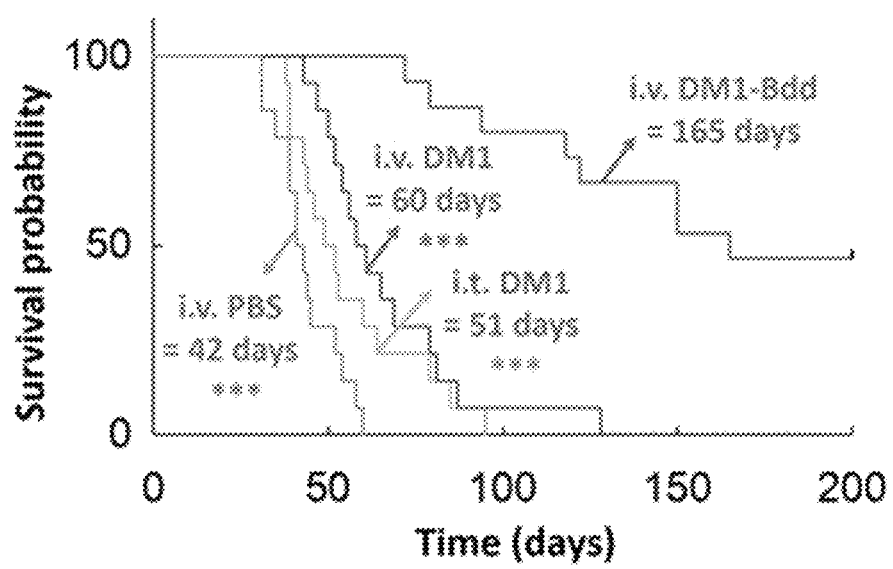
Figure 5H:
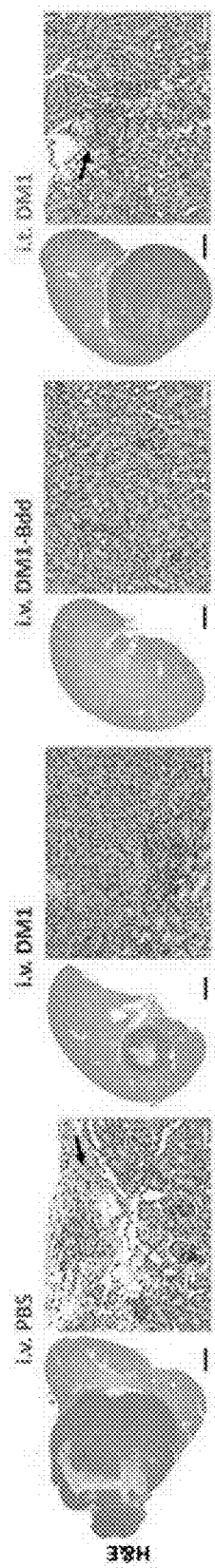

DM1-Bdd for treating renal carcinoma was evaluated using a syngeneic mouse model for the studies, which involved a surgical implantation of Renca cells (stably transduced with GFP and Luc) into the capsule of the right kidney of BALB/c mice (FIG. 5a). The tumor growth was aggressive. A tumor mass of a substantial size developed as early as 1 week after implantation (FIG. 5b). Imaging studies showed that i.v. DM1-Bdd was not only able to inhibit tumor progression (FIGS. 5c and d) but also reduced tumor size, as shown by decreased bioluminescence signals in the majority of the animals during the treatment (FIG. 5e). There was 50% of survival after 160 days (FIGS. 5f and g). On the other hand, all animals treated with either i.v. or i.t. DM1 died. In a separate experiment, histological examination of the animals' kidneys one week after completing the treatment course was performed (FIG. 5h). Minimal tumor was present in animals treated with i.v. DM1-Bdd, whereas tumors of animals treated with DM1 or PBS control were large and accompanied with an infiltration of mononuclear cells. Overall, the UDD approach was anatomically flexible and could be used for treating tumors located at the upper urinary tract.

Example 6: Toxicity Profile

Figure 6A:
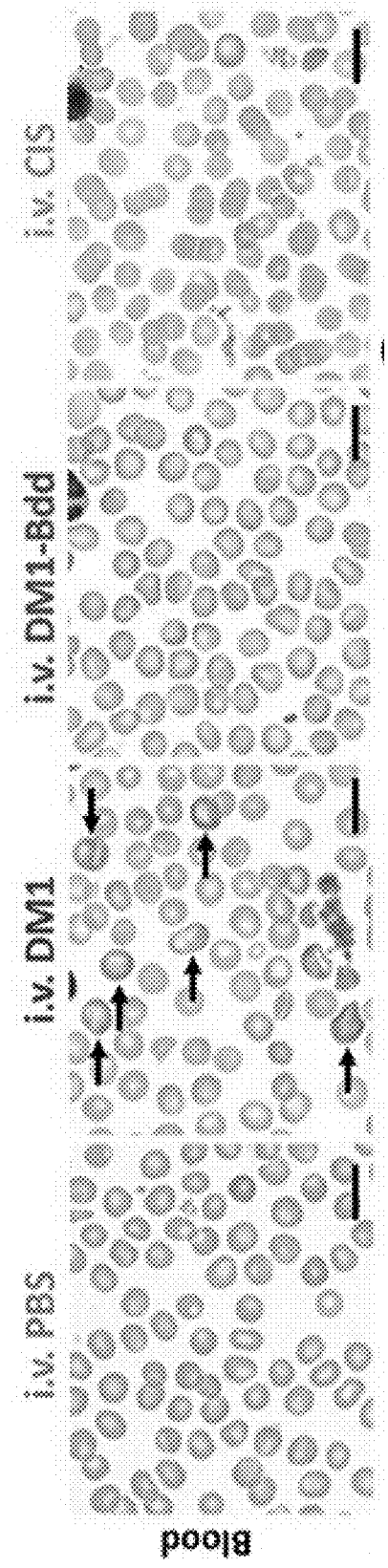
FIGS. 6A-D. DM1-Bdd displays a safe toxicity profile.
Figure 6B:
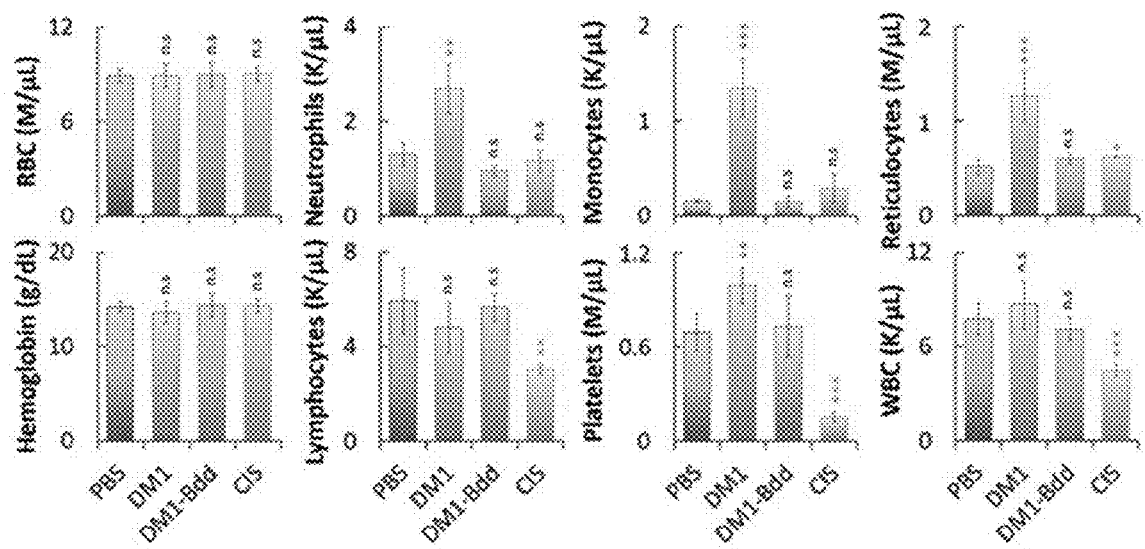
Figure 6C:
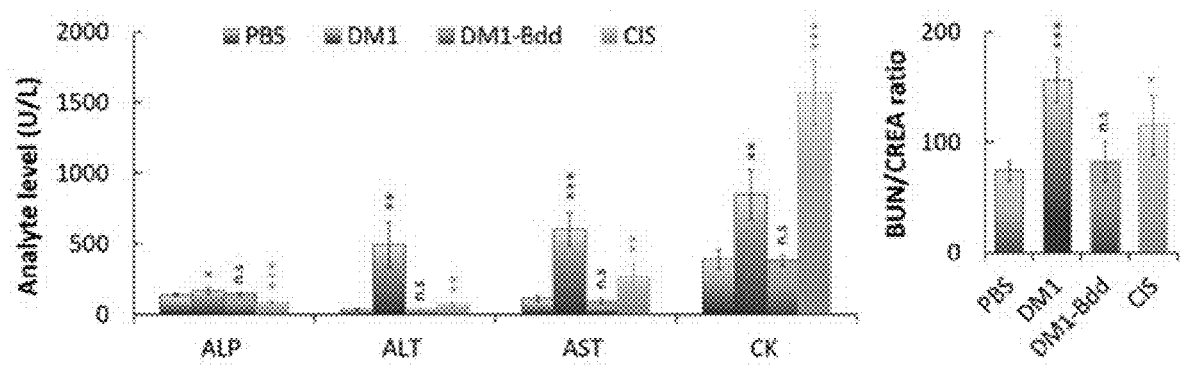
Figure 6D:
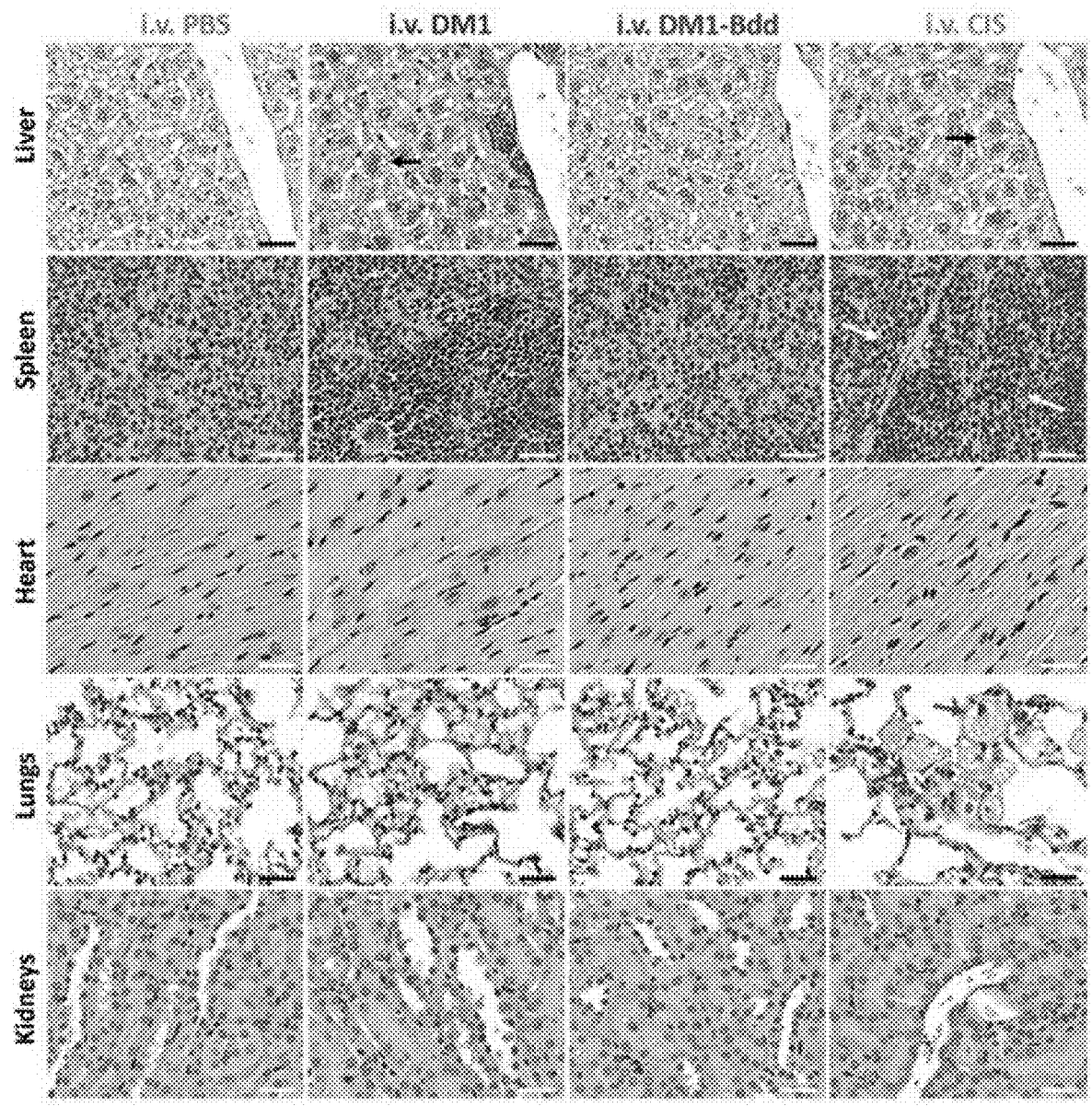
Figure 12:
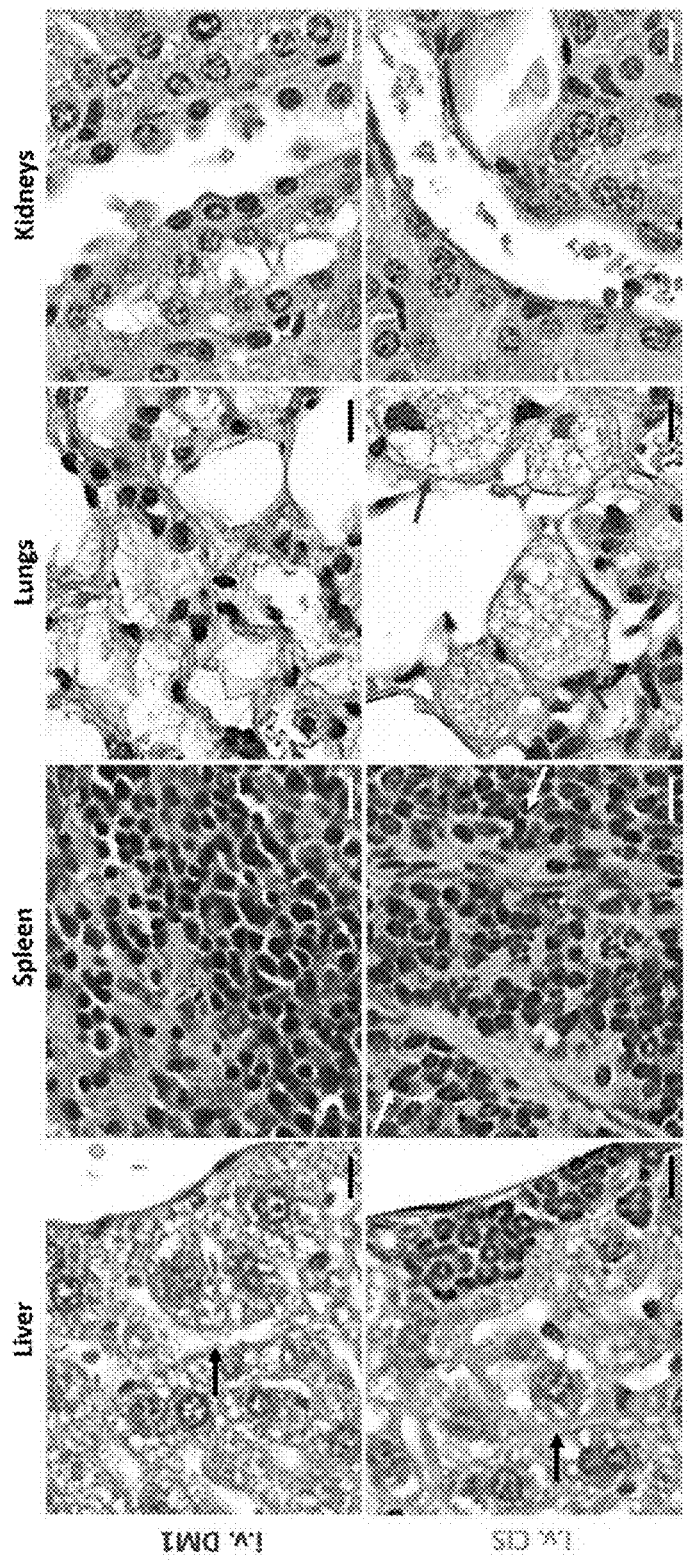
FIG. 12. High magnification images of the major organ sections (liver, spleen, lungs, and kidneys) from the animals administered with i.v. DM1 (0.75 mg/kg) and i.v. CIS (10 mg/kg) as a positive control, weekly for 3 weeks. The sections were stained with H&E. Black arrows indicate the increased of hepatocyte mitotic activity in liver. Blue arrows show enhanced hepatic and splenic extramedullary hematopoiesis (EMH). The area in between white arrows indicates depletions of erythrocytes and EMH elements in the red pulp of the spleen. Red arrows highlight the presence of large and foamy macrophages in the alveoli. Yellow and green arrows indicate flattened renal tubular cells and necrotic sloughed debris of dying cells contained within the lumen, respectively. Scale bar is 10 m.

The toxicity profile of DM1-Bdd in healthy animals after completing 3 weeks of weekly treatments was assessed. DM1-Bdd did not affect the red blood cell, leukocyte, or platelet counts or morphologic features (FIGS. 6a-b and FIG. 10). On the other hand, DM1 induced reticulocytosis without apparent anemia, and an inflammatory response characterized by increased proportions of neutrophils, monocytes, and platelets. The positive control CIS was also toxic, as evidenced by thrombocytopenia and lymphopenia. Serum biochemical analysis to assess for liver injury and renal function were also performed. DM1-Bdd was not hepatotoxic, with no significant alteration in the release of ALP, ALT, and AST (FIG. 6c and FIG. 11). Importantly, the urea nitrogen/creatinine ratio was normal, suggesting that DM1-Bdd did not affect renal clearance of nitrogenous waste. Histopathologic studies further confirmed that there was no morphological evidence of injury in the liver, spleen, heart, lungs, or kidneys of the animals treated with DM1-Bdd (FIG. 6d and FIG. 12). In contrast, the biochemical testing showed that both DM1 and CIS induced hepatic and renal toxicity, as shown by increases in ALT and AST activities and BUN/creatinine ratios (FIG. 6c). They also induced muscle injury (CK activity), which would partly explain the increases in the AST activity. Histologic examination also revealed that CIS caused degeneration and necrosis of the proximal renal tubules, lung inflammation, and depletion of both erythrocytes and extramedullary hematopoiesis (EMH) in spleen (FIG. 6d and FIG. 12). Animals treated with DM1 showed similar renal damage, but to a lesser degree. Increased splenic and hepatic EMH with DM1 were also observed, which may explain the observed reticulocytosis in the treated animals.

DISCUSSION

Most chemotherapeutics, which are toxic to healthy and cancer cells, are given by infusion so that they can be continuously administered at a higher total dose over a longer period of time. The goal is to achieve more effective treatment to improve patient tolerance to off-target toxicities by maintaining the drug's plasma concentration at a certain level and prolonging the tumor exposure to the drug. The present study aimed to promote, rather than reduce, a drug's clearance as a non-invasive alternative of ITC. Many bioactive peptides have been approved for treating various diseases, including cancer, diabetes, and cardiovascular disease. Without chemical modifications, peptides have a short circulating half-life of several minutes. They are rapidly degraded by protease enzymes and eliminated by renal filtration. In the present study it was recognized that a peptide's rapid renal clearance could be advantageous as a drug carrier to dispose most systemically administered drugs in urine for treating NMIBC and reducing the unwanted systemic side-effects. In the present invention a UDD approach was introduced by using a bio-inert, negatively charged peptide (Bdd) with minimal uptake by the recticuloendothelial system and other organs as well as to be exclusively excreted into the urine. Bdd was employed for delivering DM1, a microtubule inhibitor. DM1 was selected as it was 100-fold more potent than commonly used ITC drugs, including MIT, DOX and CIS, against a panel of BC cell lines. Further, conjugating the drug to the Bdd peptide did not compromise cytotoxicity.

In terms of therapeutic efficacy, i.v.-administered peptide-DM1 conjugate (DM1-Bdd) improved the overall survival in mice with BC compared to conventional i.t. MIT (FIG. 4h). It was also more effective compared to the same treatment given by i.t. (FIGS. 4f-i). The improved efficacy was expected given that animals did not need to void shortly after i.v. injection (FIG. 4a). Promoting renal clearance could reduce a drug's off-target toxicity. DM1-Bdd did not induce unwanted toxicity (FIG. 6). In contrast, animals treated with DM1 or CIS showed evidences of hepatic and renal injury. The flexibility of UDD approach in reducing drug-induced toxicity, by using aldox-Bdd for BC treatment was also demonstrated. Unlike free DOX that caused mortality, improved survival was observed in those animals treated with aldox-Bdd (FIG. 9). However, compared to DM1-Bdd, the aldox-Bdd treatment only slowed down the cancer progression and did not eliminate tumors in individual animals. The result was not unexpected since DM1 is more potent than DOX (FIG. 3c).

ITC is a local treatment that only covers tumors in the bladder as the drug solution cannot reach the upper urinary tract. DM1-Bdd is administered through i.v. injection. This, together with the rapid renal clearance, should allow drugs to flush the entire URS. DM1-Bdd was applied for treating renal carcinomas and it was found that DM1-Bdd offered a significant survival benefit compared to the free drug. In fact, approximately 50% of the animals lack gross or histologic evidence of the tumor one week after completing the treatment course. Intravenous drug administration will thus allow more comprehensive coverage of the URS when used for treating BC, as tumors can extend, migrate into, or recur throughout the entire urothelium, including the renal pelvis and the ureter where 8-12% of the urothelial carcinomas originate from. Currently, when treating patients with renal pelvic or ureteral tumors, surgeons are often left with no choice but to remove the entire kidney and ureter (even when the tumors are non-invasive) to prevent disease recurrence for URS tumors. DM1-Bdd can potentially be a kidney-sparing treatment option for patients with upper tract urothelial cancers.

A drawback of ITC is the poor patient compliance rate (16-30%). Patients receiving ITC need to be catheterized weekly by trained personnel in hospital/clinic. In contrast, i.v. DM1-Bdd treatment is non-invasive, which can avoid complications associated with catheterization procedures and improving patient's quality of life and compliance. The lifetime management of BC is costly, which requires repeated treatments because of its high recurrence rate. Systemic administration of a chemotherapeutic, such as DM1-Bdd, will likely reduce hospitalization costs.

Overall, a UDD approach has been developed that could minimize non-specific accumulation in other organs and offer a comprehensive treatment by supplying drug to the entire URS, as a more effective alternative to ITC. The developed DM1-Bdd is clinically translatable. The FDA has approved many peptides for treating different cancers. The employed DM1 is an active pharmacophore already used in antibody-drug conjugates, such as Herceptin-DM1 (T-DM1), for breast cancer treatment.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. A method of treating a condition selected from kidney, urinary tract or bladder cancer cancer, a urinary tract infection, overactive bladder, urinary incontinence, interstitial cystitis and kidney stones comprising administering to a patient in need thereof a compound represented by formula (I):

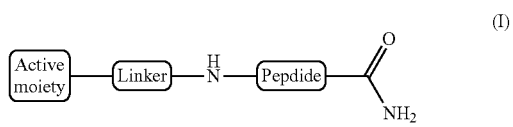

or a pharmaceutically acceptable salt thereof, wherein:
the active moiety is a therapeutic agent; and
the peptide is negatively charged at physiological pH and comprises a sequence:

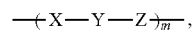

wherein:
one of X, Y and Z is a β-amino acid residue;
two of X, Y and Z are independently α-amino acid residues that each have at least one side chain that comprises a carboxylic acid group;
each α-amino acid residue is independently of D or L stereochemistry; and
m is from 2 to 10.

2. The method of claim 1, wherein the condition is kidney, urinary tract, bladder cancer.

3. The method of claim 2, wherein the bladder cancer is selected from non-muscle invasive bladder cancer and urothelial carcinoma.

4. The method of claim 1, wherein the compound is administered intravenously.

5. The method of claim 1, wherein the peptide has a zeta potential of from about −30 mV to about +20 mV at physiological pH.

6. The method of claim 1, wherein the linker comprises one or more groups selected from amide, imide, thiourea, thioether, disulfide, alkyl, aryl, polyether, hydrazone, ester, carbonate, ketal and silyl ether.

7. The method of claim 1, wherein the β-amino acid residue does not comprise an ionizable side chain.

8. The method of claim 1, wherein the β-amino acid residue is a β-alanine residue.

9. The method of claim 1, wherein X is a β-alanine residue.

10. The method of claim 1, wherein each α-amino acid residue is independently selected from an aspartic acid residue and a glutamic acid residue.

11. The method of claim 1, wherein at least one α-amino acid residue is an unnatural amino acid residue having at least two side chain carboxylic acid groups.

12. The method of claim 11, wherein the unnatural α-amino acid residue is selected from a 2-aminoethane-1,1,2-tricarboxylic acid residue and a 2-aminopropane-1,2,3-tricarboxylic acid residue.

13. The method of claim 10, wherein each Y and Z is an aspartic acid residue.

14. The method of claim 1, wherein X, Y and Z are each independently selected from a β-alanine residue, an aspartic acid residue and a glutamic acid residue.

15. The method of claim 1, wherein the linker comprises a group selected from:

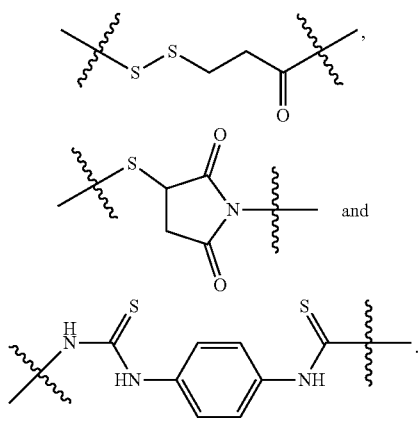

and

16. The method of claim 1, wherein the therapeutic agent is selected from an anticancer agent, an antibiotic, an agent that treats overactive bladder, an agent that treats urinary incontinence, an agent that treats interstitial cystitis and an agent that treats kidney stones.

17. The method of claim 16, wherein the therapeutic agent is an anticancer agent selected from mertansine, doxorubicin, dasatinib, cisplatin, mitomycin, gemcitabine and paclitaxel.

18. The method of claim 1, wherein,
X is a β-alanine residue; and Y and Z are D-aspartic acid residues, or
X is a β-alanine residue; Y and Z are D-aspartic acid residues; and m is 4, or
X is a β-alanine residue; Y and Z are D-aspartic acid residues; m is 4; the linker comprises a disulfide group; and the active moiety is mertansine.

19. The method of claim 1, wherein the compound is:

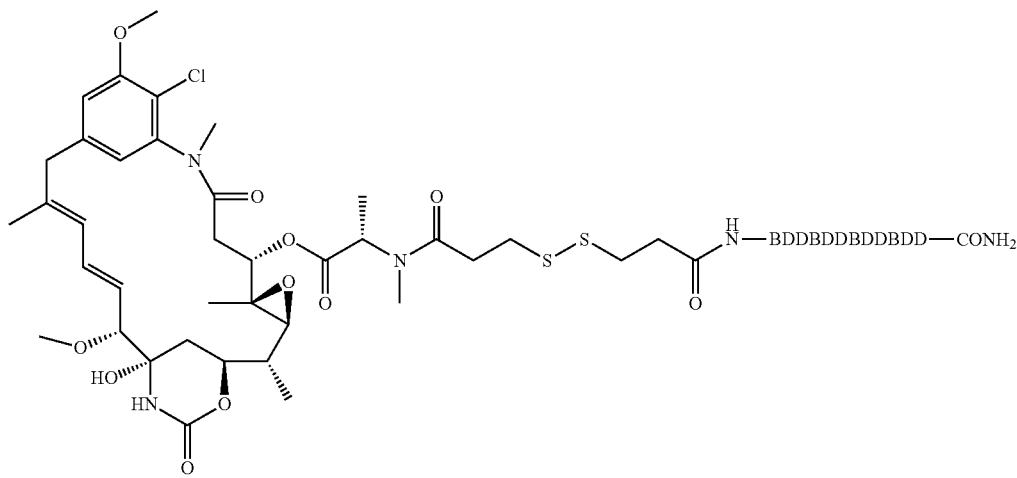

or a pharmaceutically acceptable salt thereof, wherein B is a β-alanine residue and D is an aspartic acid residue of D or L configuration, or

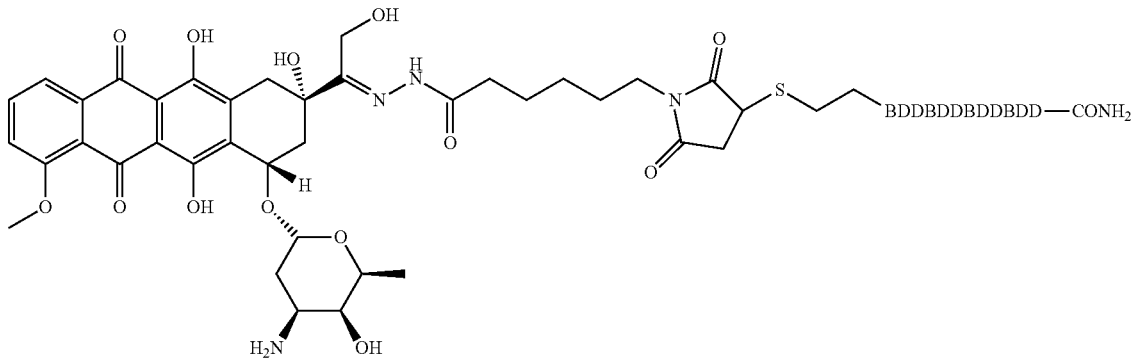

or a pharmaceutically acceptable salt thereof, wherein B is a β-alanine residue and D is an aspartic acid residue of D or L configuration.

\* \* \* \* \*

UNITED STATES PATENT AND TRADEMARK OFFICE
CERTIFICATE OF CORRECTION

PATENT NO. : 12,263,223 B2
APPLICATION NO. : 18/095753
DATED : April 1, 2025
INVENTOR(S) : Shek Hang Benedict Law et al.

Page 1 of 1

It is certified that error appears in the above-identified patent and that said Letters Patent is hereby corrected as shown below:

In the Claims

In Claim 1, at Column 37, Line 66, please replace:
"cancer cancer"
With:
-- cancer --.

Signed and Sealed this
Twenty-third Day of December, 2025

John A. Squires
*Director of the United States Patent and Trademark Office*